US012648780B2

(12) United States Patent
Johnson et al.

(10) Patent No.: US 12,648,780 B2
(45) Date of Patent: Jun. 9, 2026

(54) TOOLS FOR CREATING A VERTEBRAL TUNNEL FOR USE IN RF ABLATION AND METHODS OF MAKING AND USING

(71) Applicant: Boston Scientific Neuromodulation Corporation, Valencia, CA (US)

(72) Inventors: Courtney Johnson, Valencia, CA (US); Eric Koji Nagaoka, Camarillo, CA (US); Jens Peter Timms, Carlsbad, CA (US); Scott Anthony Silveus, Carmel, IN (US); Kevin Peng Wang, Fremont, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 300 days.

(21) Appl. No.: 18/373,586

(22) Filed: Sep. 27, 2023

(65) Prior Publication Data

US 2024/0108361 A1 Apr. 4, 2024

Related U.S. Application Data

(60) Provisional application No. 63/413,122, filed on Oct. 4, 2022.

(51) Int. Cl.
*A61B 17/00* (2006.01)
*A61B 17/16* (2006.01)
(Continued)

(52) U.S. Cl.
CPC ...... *A61B 17/1671* (2013.01); *A61B 17/3423* (2013.01); *A61B 17/3472* (2013.01); *A61B 2017/00477* (2013.01)

(58) Field of Classification Search
CPC ............ A61B 17/1671; A61B 17/3423; A61B 17/3472; A61B 17/1642; A61B 17/1604;
(Continued)

(56) References Cited

U.S. PATENT DOCUMENTS 4,411,266 A 10/1983 Cosman
4,565,200 A 1/1986 Cosman
(Continued)

FOREIGN PATENT DOCUMENTS

WO 99/40859 8/1999
WO 99/40860 8/1999
(Continued)

OTHER PUBLICATIONS

Hemostasis Vales—Qosina—URL: hllps://www.qosina.com/vascular-access-hemostasis-valves 9 pages—retrieved Nov. 13, 2019.
(Continued)

*Primary Examiner* — Tan-Uyen T Ho
*Assistant Examiner* — Lindsey R. Rivers
(74) *Attorney, Agent, or Firm* — Branch Partners PLLC; Bruce E. Black

(57) ABSTRACT

A tool arrangement for forming a tunnel in a vertebra to perform nerve ablation includes a tamp having a distal end portion that includes a tip for creating the tunnel in the vertebra and a curvable portion to direct the tip along a curved path within the vertebra; a first cannula including a cannula body that is straight along an entire length of the cannula body and configured to receive the curvable portion of the tamp and straighten the curvable portion; and a tool hub including a stationary cannula attachment coupled to the first cannula and a movable head coupled to the tamp and configured to move toward or away from the stationary cannula attachment to extend or retract, respectively, the curvable portion of the tamp from or into, respectively, the first cannula.

14 Claims, 13 Drawing Sheets

(51) Int. Cl.
*A61B 17/34* (2006.01)
*A61B 18/00* (2006.01)
*A61B 18/14* (2006.01)
*A61B 90/00* (2016.01)

(58) Field of Classification Search
CPC .......... A61B 2017/00477; A61B 2017/00323;
A61B 2017/00331; A61B 2017/00867;
A61B 18/148; A61B 2018/00339; A61B
2018/00577; A61B 2090/034
See application file for complete search history.

(56) References Cited

U.S. PATENT DOCUMENTS

| | | | |
|---|---|---|---|
| 4,566,454 A | 1/1986 | Mehl et al. |
| 4,597,379 A | 7/1986 | Kihn et al. |
| 4,727,874 A | 3/1988 | Bowers et al. |
| 4,807,620 A | 2/1989 | Strul et al. |
| 5,360,009 A | 11/1994 | Herskovitz |
| 5,433,739 A | 7/1995 | Sluijter et al. |
| 5,571,147 A | 11/1996 | Sluijter et al. |
| 5,728,143 A | 3/1998 | Gough et al. |
| 5,769,847 A | 6/1998 | Panescu et al. |
| 5,951,546 A | 9/1999 | Lorentzen |
| 5,983,141 A | 11/1999 | Sluijter et al. |
| 6,070,845 A | 6/2000 | Herskovitz |
| 6,080,149 A | 6/2000 | Huang et al. |
| 6,104,959 A | 8/2000 | Spertell |
| 6,161,048 A | 12/2000 | Sluijter et al. |
| 6,203,524 B1 | 3/2001 | Burney et al. |
| 6,245,065 B1 | 6/2001 | Panescu et al. |
| 6,246,912 B1 | 6/2001 | Sluijter et al. |
| 6,259,952 B1 | 7/2001 | Sluijter et al. |
| 6,301,506 B1 | 10/2001 | Den Boer et al. |
| 6,321,120 B1 | 11/2001 | Surbeck et al. |
| 6,341,429 B1 | 1/2002 | Herskovitz |
| 6,397,106 B1 | 5/2002 | DeBrouse |
| 6,402,739 B1 | 6/2002 | Neev |
| 6,428,537 B1 | 8/2002 | Swanson et al. |
| 6,440,127 B2 | 8/2002 | McGovern et al. |
| 6,447,505 B2 | 9/2002 | McGovern et al. |
| 6,482,204 B1 | 11/2002 | Lax et al. |
| 6,517,534 B1 | 2/2003 | McGovern et al. |
| 6,530,922 B2 | 3/2003 | Cosman et al. |
| 6,692,493 B2 | 2/2004 | McGovern et al. |
| 6,743,226 B2 | 6/2004 | Cosman et al. |
| 6,843,789 B2 | 1/2005 | Goble |
| 6,853,864 B2 | 2/2005 | Litovitz |
| 6,869,430 B2 | 3/2005 | Balbierz et al. |
| 7,363,071 B2 | 4/2008 | Damasco et al. |
| 7,522,953 B2 | 4/2009 | Kaula et al. |
| 7,553,309 B2 | 6/2009 | Buysse et al. |
| 7,574,257 B2 | 8/2009 | Rittman, III |
| 7,725,155 B2 | 5/2010 | Dowlatshahi |
| 7,749,218 B2 | 7/2010 | Pellegrino et al. |
| 7,799,024 B2 | 9/2010 | Randall |
| 8,123,782 B2 | 2/2012 | Altarac et al. |
| 8,128,662 B2 | 3/2012 | Altarac et al. |
| 8,273,108 B2 | 9/2012 | Altarac et al. |
| 8,277,488 B2 | 10/2012 | Altarac et al. |
| 8,292,922 B2 | 10/2012 | Altarac et al. |
| 8,361,607 B2 | 1/2013 | Higuchi et al. |
| 8,425,559 B2 | 4/2013 | Altarac et al. |
| 8,512,333 B2 | 8/2013 | Epstein et al. |
| 8,518,037 B2 | 8/2013 | Young |
| 8,613,747 B2 | 12/2013 | Altarac et al. |
| 8,808,284 B2 | 8/2014 | Pellegrino et al. |
| 8,864,828 B2 | 10/2014 | Altarac et al. |
| 8,945,183 B2 | 2/2015 | Altarac et al. |
| 8,979,830 B2 | 3/2015 | Hennings |
| 8,992,522 B2 | 3/2015 | Pellegrino et al. |
| 9,039,701 B2 | 5/2015 | Pellegrino et al. |
| 9,119,680 B2 | 9/2015 | Altarac et al. |
| 9,155,570 B2 | 10/2015 | Altarac et al. |
| 9,155,572 B2 | 10/2015 | Altarac et al. |

| | | | |
|---|---|---|---|
| 9,161,783 B2 | 10/2015 | Altarac et al. |
| 9,173,676 B2 | 11/2015 | Pellegrino et al. |
| 9,186,186 B2 | 11/2015 | Reglos et al. |
| 9,393,055 B2 | 7/2016 | Altarac et al. |
| 9,532,812 B2 | 1/2017 | Altarac et al. |
| 9,572,603 B2 | 2/2017 | Altarac et al. |
| 9,717,552 B2 | 8/2017 | Cosman et al. |
| 9,861,398 B2 | 1/2018 | Altarac et al. |
| 9,949,782 B2 | 4/2018 | Hagg et al. |
| 9,956,011 B2 | 5/2018 | Altarac et al. |
| 9,956,032 B1 | 5/2018 | Cosman et al. |
| 10,080,587 B2 | 9/2018 | Altarac et al. |
| 10,111,703 B2 | 10/2018 | Cosman, Jr. et al. |
| 10,136,937 B1 | 11/2018 | Cosman, Jr. et al. |
| 10,136,942 B1 | 11/2018 | Cosman, Jr. et al. |
| 10,136,943 B1 | 11/2018 | Cosman, Jr. et al. |
| 10,166,047 B2 | 1/2019 | Altarac et al. |
| 10,194,971 B2 | 2/2019 | Wegrzyn, III et al. |
| 10,342,606 B2 | 7/2019 | Cosman et al. |
| 10,357,258 B2 | 7/2019 | Patel et al. |
| 10,363,063 B2 | 7/2019 | Cosman |
| 10,420,591 B2 | 9/2019 | Snell et al. |
| 10,463,423 B2 | 11/2019 | Sutton et al. |
| 10,478,246 B2 | 11/2019 | Pellegrino et al. |
| 10,517,611 B2 | 12/2019 | Patel et al. |
| 10,548,654 B2 | 2/2020 | Curley |
| 10,588,687 B2 | 3/2020 | Cosman, Jr. et al. |
| 10,610,267 B2 | 4/2020 | Altarac et al. |
| 10,631,915 B1 | 4/2020 | Cosman |
| 10,639,098 B2 | 5/2020 | Cosman et al. |
| 10,639,101 B2 | 5/2020 | Cosman et al. |
| 10,653,456 B2 | 5/2020 | Altarac et al. |
| 10,709,502 B2 | 7/2020 | Viswanathan |
| 10,835,295 B2 | 11/2020 | Altarac et al. |
| 10,835,297 B2 | 11/2020 | Altarac et al. |
| 11,013,539 B2 | 5/2021 | Altarac et al. |
| 11,058,455 B2 | 7/2021 | Cosman, Jr. |
| 11,076,893 B2 | 8/2021 | Altarac et al. |
| 11,116,585 B2 | 9/2021 | Lyons et al. |
| 11,207,100 B2 | 12/2021 | Donovan et al. |
| 11,229,461 B2 | 1/2022 | Altarac et al. |
| 2002/0077683 A1 | 6/2002 | Westlund et al. |
| 2002/0156472 A1 | 10/2002 | Lee et al. |
| 2002/0165531 A1 | 11/2002 | Goble |
| 2003/0032951 A1 | 2/2003 | Rittman et al. |
| 2003/0212390 A1 | 11/2003 | Chen et al. |
| 2005/0065509 A1 | 3/2005 | Coldwell et al. |
| 2005/0277918 A1 | 12/2005 | Shah et al. |
| 2006/0052850 A1 | 3/2006 | Darmos et al. |
| 2007/0032835 A1 | 2/2007 | Rittman |
| 2008/0195152 A1 | 8/2008 | Altarac et al. |
| 2008/0200972 A1 | 8/2008 | Rittman et al. |
| 2008/0262490 A1 | 10/2008 | Williams |
| 2009/0138046 A1 | 5/2009 | Altarac et al. |
| 2010/0114093 A1 | 5/2010 | Mahapatra et al. |
| 2010/0222747 A1 | 9/2010 | Wenchell et al. |
| 2010/0249750 A1 | 9/2010 | Racz et al. |
| 2011/0028836 A1 | 2/2011 | Ranpura et al. |
| 2011/0288540 A1 | 11/2011 | Wright et al. |
| 2011/0301578 A1 | 12/2011 | Muniz-Medina et al. |
| 2012/0203064 A1 | 8/2012 | Wynberg |
| 2013/0345699 A1 | 12/2013 | Brannan et al. |
| 2014/0066917 A1 | 3/2014 | Cosman, Jr. et al. |
| 2014/0081260 A1 | 3/2014 | Cosman, Jr. et al. |
| 2014/0121658 A1 | 5/2014 | Cosman, Jr. et al. |
| 2014/0276800 A1 | 9/2014 | Batchelor et al. |
| 2015/0182234 A1 | 7/2015 | Mahoney et al. |
| 2015/0297282 A1 | 10/2015 | Cadouri |
| 2015/0305799 A1 | 10/2015 | Trieu |
| 2016/0206362 A1 | 7/2016 | Mehta et al. |
| 2016/0242822 A1 | 8/2016 | Altarac et al. |
| 2016/0278791 A1 | 9/2016 | Pellegrino et al. |
| 2017/0004951 A1 | 1/2017 | Weisz et al. |
| 2017/0049514 A1 | 2/2017 | Cosman |
| 2018/0318061 A1 | 11/2018 | Clarke et al. |
| 2019/0110833 A1 | 4/2019 | Pellegrino et al. |
| 2019/0201057 A1 | 7/2019 | Altarac et al. |
| 2019/0223948 A1 | 7/2019 | Stewart et al. |
| 2019/0239941 A1 | 8/2019 | Schorr et al. |

(56)    References Cited

U.S. PATENT DOCUMENTS

| | | | |
|---|---|---|---|
| 2020/0038091 A1 | 2/2020 | Cao et al. | |
| 2020/0038096 A1 | 2/2020 | Schepis et al. | |
| 2020/0139144 A1 | 5/2020 | Cosman et al. | |
| 2020/0146744 A1 | 5/2020 | Defosset et al. | |
| 2020/0281646 A1 | 9/2020 | Pellegrino et al. | |
| 2020/0330153 A1 | 10/2020 | Cosman, Jr. et al. | |
| 2020/0367871 A1 * | 11/2020 | Van Hoven | A61F 2/2466 |
| 2020/0383707 A1 | 12/2020 | Kidman et al. | |
| 2021/0038298 A1 | 2/2021 | Scott et al. | |
| 2021/0100592 A1 | 4/2021 | Seifert et al. | |
| 2021/0121224 A1 | 4/2021 | Ranpura et al. | |
| 2021/0236191 A1 | 8/2021 | Wang et al. | |
| 2021/0322063 A1 | 10/2021 | Altarac et al. | |
| 2021/0369394 A1 | 12/2021 | Braido et al. | |
| 2021/0393315 A1 | 12/2021 | McGregor et al. | |
| 2022/0061894 A1 | 3/2022 | Altarac et al. | |
| 2022/0202484 A1 | 6/2022 | Wang et al. | |
| 2022/0202485 A1 | 6/2022 | Marusich et al. | |
| 2022/0226039 A1 | 7/2022 | Wang | |
| 2022/0323147 A1 | 10/2022 | Hata et al. | |
| 2022/0401085 A1 | 12/2022 | Cosman, Jr. | |
| 2024/0108361 A1 | 4/2024 | Johnson et al. | |
| 2024/0108394 A1 | 4/2024 | Bates et al. | |
| 2024/0245445 A1 | 7/2024 | Bates | |
| 2024/0245449 A1 | 7/2024 | Bates | |
| 2024/0277384 A1 | 8/2024 | Malinowski | |
| 2024/0423687 A1 | 12/2024 | Johnson et al. | |
| 2024/0423701 A1 | 12/2024 | Johnson et al. | |

FOREIGN PATENT DOCUMENTS

| | | | |
|---|---|---|---|
| WO | 00/59394 | 10/2000 | |
| WO | 2007121143 | 10/2007 | |
| WO | WO-2014071161 A1 * | 5/2014 | ......... A61B 17/1671 |
| WO | 2014130031 | 8/2014 | |
| WO | WO-2016162869 A2 * | 10/2016 | ......... A61B 17/1617 |
| WO | WO-2021050767 A1 * | 3/2021 | ........... A61B 18/082 |
| WO | WO2022011115 | 1/2022 | |

OTHER PUBLICATIONS

*Coolief* Cooled Radio Frequency Kit—Instructions for Use Halyard—dated Feb. 9, 2017—8 pages.

Cobra R-F™—Epimed—URL: https://www.epimed.com/products/cobra-r-f/—retrieved Jan. 27, 2021.

Hyso et al., "Epimed Launches "Cobra" R-F™ Dual Use Radiofrequency Cannula" Cision—PR Web—Jan. 17, 2019 3 pages.

"Venom cannula and electrode system"—Stryker—retrieved Sep. 8, 2020 URL: https://www.stryker.com/us/en/interventional-spine/products/venom-cannula-and-electrode-system.html.

"RF Trident™ Cannulae" Diros Technology Inc. Nov. 11, 2017 URL: https://web.archive.org/web/20171117054945/https://dirostech.com/product-details/rf-tridenttrident-hybrid-cannulae/.

Cedeno et al., "Comparisons of Lesion Volumes and Shapes Produced by a Radiofrequency System with a Cooled, a Protruding, or a Monopolar Probe" Pain Physician 2017; 20:E915-E922 •ISSN 2150-1149.

Correspondence from Department of Health and Human Services to George Darmos at Diros Technology, Inc.—dated Jul. 30, 2015—11 pages.

Correspondence from Department of Health and Human Services to Christina McKee—dated Mar. 28, 2013; 7 pages.

Cosman et al. "Theoretical Aspects of Radiofrequency Lesions in the Dorsal Root Entry Zone," Neurosurgery, vol. 15, No. 6, p. 945-950 (1984).

U.S. Appl. No. 18/373,626, filed Sep. 27, 2023.

Rhame EE, Levey KA, Gharibo CG. Successful treatment of refractory pudendal neuralgia with pulsed radiofrequency. Pain Physician. May-Jun. 2009;12(3):633-8. PMID: 19461829.

Todorov L. Pulsed radiofrequency of the sural nerve for the treatment of chronic ankle pain. Pain Physician. May-Jun. 2011;14(3):301-4. PMID: 21587334.

International Search Report and Written Opinion for PCT Application No. PCT/US2023/033828 mailed Jan. 30, 2024.

* cited by examiner

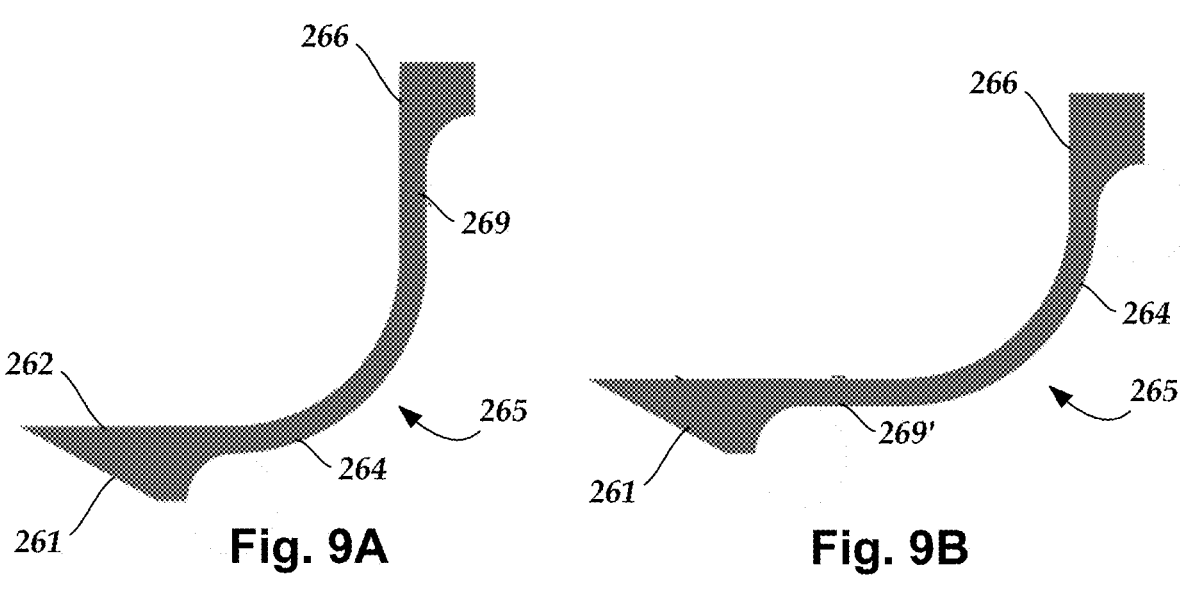
Fig. 9A
Fig. 9B
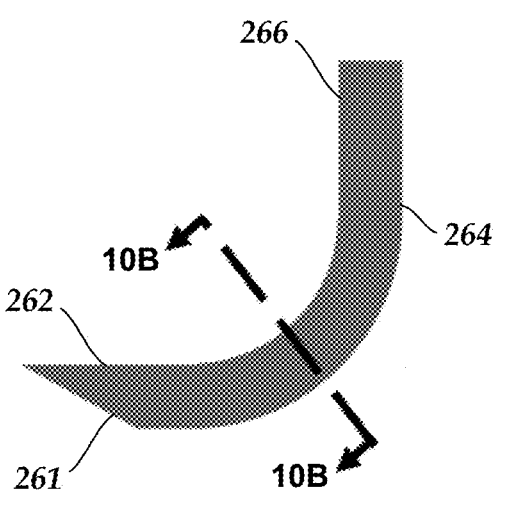
Fig. 10A
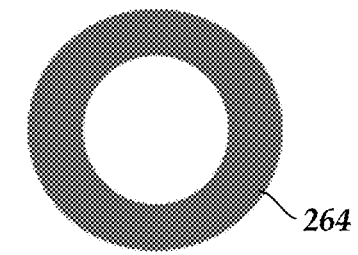
Fig. 10B
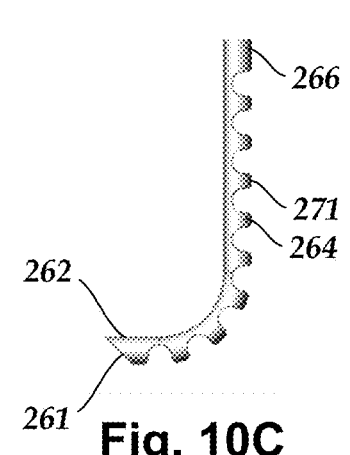
Fig. 10C
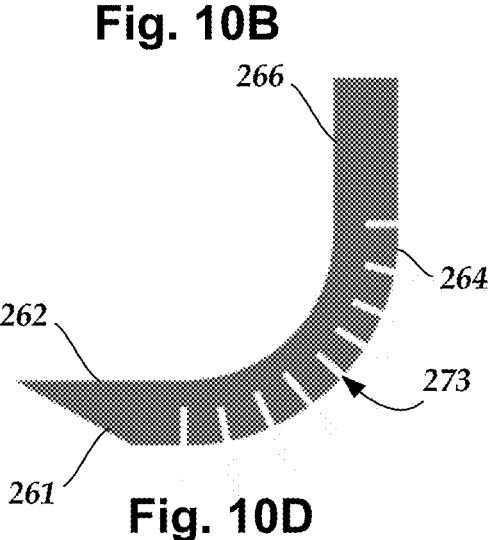
Fig. 10D

TOOLS FOR CREATING A VERTEBRAL TUNNEL FOR USE IN RF ABLATION AND METHODS OF MAKING AND USING

CROSS-REFERENCE TO RELATED APPLICATIONS

This application claims the benefit under 35 U.S.C. § 119(e) of U.S. Provisional Patent Application Ser. No. 63/413,122, filed Oct. 4, 2022, which is incorporated herein by reference.

FIELD

The present disclosure is directed to the area of radiofrequency (RF) ablation and methods of preparing for RF ablation. The present disclosure is also directed to a tool for creating a vertebral tunnel for use in RF ablation, as well as methods of making and using the same.

BACKGROUND

Radiofrequency (RF) generators and electrodes can be used for pain relief or functional modification. Radiofrequency ablation (RFA) is a safe, proven means of interrupting pain signals, such as those coming from irritated facet joints in the spine, genicular nerves in the knee, and femoral and obturator nerves in the hip. Radiofrequency current is used to heat up a small volume of nerve tissue, thereby interrupting pain signals from that specific area. Radiofrequency ablation is designed to provide long-lasting pain relief.

Basivertebral nerve ablation (BVN) can be used to, for example, treat discogenic back pain or other conditions. The basivertebral nerve is ablated using RF energy. Typically, the root of the basivertebral nerve is located in the near center of the patient's vertebral body (for example, approximately 50%/50% cranial-to-caudal, 50%/50% left-to-right, and 60%-75%/25%-40% anterior-to-posterior.) In at least some embodiments, to access this ablation target the clinician can traverse the pedicle of the vertebrae (either left or right side) and then make a turn towards midline. Instead of trans-pedicular, an extrapedicular approach can be used. A tunnel is created through the bone and then an electrode is inserted into the bone for ablation. It can be challenging to create a curved tunnel within the vertebrae to access the basivertebral nerve.

BRIEF SUMMARY

One aspect is a tool arrangement for forming a tunnel in a vertebra to perform nerve ablation. The tool arrangement including a tamp having a distal end portion and a proximal end portion, wherein the distal end portion includes a tip configured for creating the tunnel in the vertebra and a curvable portion coupled to the tip and configured to direct the tip along a curved path within the vertebra; a first cannula including a cannula body defining a lumen through which the tamp is extendable, wherein the cannula body is straight along an entire length of the cannula body and the first cannula is configured to receive the curvable portion of the tamp and straighten the curvable portion when the curvable portion is received in the first cannula; and a tool hub including a stationary cannula attachment coupled to the first cannula and a movable head coupled to the tamp and configured to move toward or away from the stationary cannula attachment to extend or retract, respectively, the curvable portion of the tamp from or into, respectively, the first cannula.

In at least some aspects, the first cannula is a tamp cannula, the tool arrangement further including an access tool having an access tool handle and an access tool cannula, wherein the access tool cannula is straight along an entire length of the access tool cannula and the access tool is configured to receive the tamp cannula within the access tool cannula.

In at least some aspects, the tool arrangement further includes an access tool having an access tool handle and the first cannula.

In at least some aspects, the tool hub further includes a rotatable collar disposed between the stationary cannula attachment and the movable head. In at least some aspects, the movable head includes a threaded post. In at least some aspects, the rotatable collar includes a lumen with a threaded portion configured to receive and interact with the threaded post of the movable head. In at least some aspects, rotating the collar moves the movable head away from or toward the stationary cannula attachment depending on a direction of rotation. In at least some aspects, the stationary cannula attachment includes a shaft and the movable head or rotatable collar slide along the shaft as the movable head moves toward the stationary cannula attachment to extend the curvable portion of the tamp out of the first cannula.

In at least some aspects, the movable head includes an impact element to receive impacts from a hammer or mallet. In at least some aspects, the curvable portion of the tamp is defined, relative to the shaft and the tip, by a cutout and is offset relative to a central axis of at least one of the shaft or the tip of the tamp. In at least some aspects, the curvable portion bends away from the cutout. In at least some aspects, the curvable portion of the tamp defines a relieved channel along the curvable portion. In at least some aspects, the tool arrangement further includes at least two pull wires attached to the tip of the tamp to manually guide the tamp in forming the tunnel.

A further aspect is a method for forming a tunnel in a vertebra to perform nerve ablation. The method includes inserting an access tool cannula of an access tool into the vertebra of a patient, wherein the access tool cannula is straight; inserting a tamp cannula of a tamp tool into the access tool cannula of the access tool, wherein the tamp cannula is straight; and operating a tool hub of the tamp tool to extend a distal end portion of a tamp out of a distal end of the tamp cannula to form the tunnel, wherein the distal end portion of the tamp includes a tip configured for creating the tunnel in the vertebra and a curvable portion coupled to the tip and configured to direct the tip along a curved path within the vertebra, wherein the curvable portion is biased to curve when outside of the tamp cannula, wherein the curvable portion is straightened within the tamp cannula prior to extending out of the distal end of the tamp cannula.

In at least some aspects, operating the tool hub includes driving a movable head of the tool hub toward a stationary cannula attachment of the tool hub, wherein the tamp is coupled to the movable head. In at least some aspects, the method further includes after forming the tunnel, operating the tool hub of the tamp tool to retract the curvable portion of the tamp into the tamp cannula and straightening the curvable portion within the tamp cannula. In at least some aspects, operating the tool hub to retract the curvable portion includes rotating a rotatable collar of the tool hub to move a movable head of the tool hub away from a stationary cannula attachment of the tool hub, wherein the tamp is coupled to the movable head.

Another aspect is a tamp tool for forming a tunnel in a vertebra to perform nerve ablation. The tamp tool includes a tamp having a distal end portion and a proximal end portion, wherein the distal end portion includes a tip configured for creating the tunnel in the vertebra and a curvable portion coupled to the tip and configured to direct the tip along a curved path within the vertebra; a tamp cannula including a cannula body defining a lumen through which the tamp is extendable, wherein the tamp cannula is configured to receive the curvable portion of the tamp, wherein the curvable portion of the tamp is biased to curve when outside of the tamp cannula; and a tool hub including a stationary cannula attachment coupled to the tamp cannula, a movable head coupled to the tamp, and a rotatable collar configured to move the movable head toward or away from the stationary cannula attachment to extend or retract, respectively, the curvable portion of the tamp from or into, respectively, the tamp cannula.

In at least some aspects, the movable head includes a threaded post and the rotatable collar includes a lumen with a threaded portion configured to receive and interact with the threaded post. In at least some aspects, the stationary cannula attachment includes a shaft and the movable head or rotatable collar slide along the shaft as the movable head moves toward the stationary cannula attachment to extend the curvable portion of the tamp out of the tamp cannula. In at least some aspects, the tamp cannula is straight and is configured to straighten the curvable portion of the tamp when the curvable portion is received in the tamp cannula.

Yet another aspect is a method for forming a tunnel in a vertebra to perform nerve ablation. The method includes inserting an access tool cannula of an access tool into the vertebra of a patient; inserting the tamp cannula of one of the tamp tools described above into the access tool cannula of the access tool; and driving the movable head of the tool hub toward the stationary cannula attachment of the tool hub to extend a distal end portion of a tamp out of a distal end of the tamp cannula to form the tunnel, wherein the distal end portion of the tamp includes a tip configured for creating the tunnel in the vertebra and a curvable portion coupled to the tip and configured to direct the tip along a curved path within the vertebra, wherein the curvable portion is biased to curve when outside of the tamp cannula.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 9A is a schematic side view of a distal portion of a fifth embodiment of a tamp with a cutout portion defining a curvable region of the tamp and a straight region between the curvable region and the shaft of the tamp;

FIG. 9B is a schematic side view of a distal portion of a sixth embodiment of a tamp with a cutout portion defining a curvable region of the tamp and a straight region between the curvable region and the tip of the tamp;

FIG. 10A is a schematic side view of a distal portion of a seventh embodiment of a tamp with a curvable region of the tamp formed using a curvable tube;

FIG. 10B is a cross-sectional view of the curvable region of the tamp of FIG. 10A;

FIG. 10C is a schematic side view of a distal portion of an eighth embodiment of a tamp with a curvable region of the tamp defined by multiple cutout teeth;

FIG. 10D is a schematic side view of a distal portion of a ninth embodiment of a tamp with a curvable region of the tamp defined by multiple microcuts;

DETAILED DESCRIPTION

The present disclosure is directed to the area of radiofrequency (RF) ablation and methods of preparing for RF ablation. The present disclosure is also directed to a tool for creating a vertebral tunnel for use in RF ablation, as well as methods of making and using the same.

Figure 1:
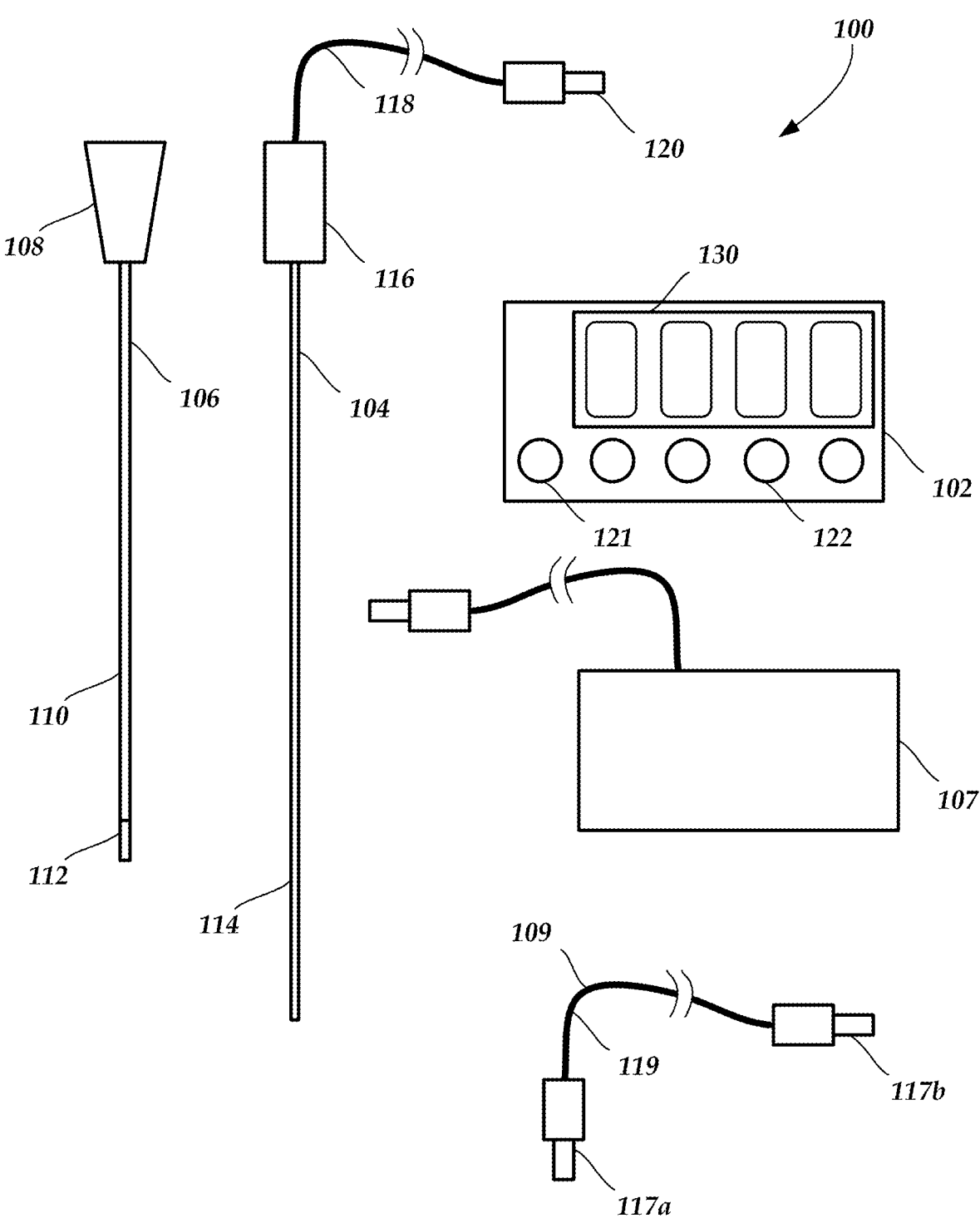
FIG. 1 is a schematic side view of components of one embodiment of a conventional RF ablation system.

FIG. 1 illustrates one embodiment of a conventional RF ablation system 100 that includes a RF generator 102, a RF electrode 104, a cannula 106, a ground pad 107, and an optional extension cable 109. The cannula 106 includes a cannula hub 108, an insulated shaft 110, and an active tip 112. The insulated shaft 110 is hollow for receiving the RF electrode 104. When inserted, the RF electrode 104 contacts, and energizes, the active tip 112 of the cannula 106 to produce RF ablation. The RF electrode 104 includes an electrode shaft 114, an electrode hub 116, a cable 118 that is electrically coupled to the electrode shaft 114, and a connector 120 for connecting to a port 122 of the RF generator 102 to energize the electrode shaft 114 via the cable 118 and connector 120. The optional adapter or extension 109 includes a cable 119 and connectors 117a, 117b for coupling the RF electrode 104 to the RF generator 102. It will be recognized that other RF ablation systems utilize the RF electrode 104 for ablation instead of, or in addition to, the cannula 106.

The RF generator 102 can include one or more ports 122 and at least one screen 130. In at least some embodiments, each port 122 is associated with a portion of the screen 130 (or a different screen) and can receive the connector 120 from an RF electrode 104. Information such as current, voltage, status, time, temperature, power, impedance, or the like or any combination thereof can be displayed on the screen 130. In at least some embodiments, each port 122 corresponds to an independent channel for operating a RF electrode 104. The RF generator 102 also includes a ground port 121 for attachment of the ground pad 107.

Examples of RF generators and RF ablation systems and methods of making and using the RF generators and RF ablation systems can be found at, for example, U.S. Pat. Nos. 9,717,552; 9,956,032; 10,111,703; 10,136,937; 10,136,942;

10,136,943; 10,194,971; 10,342,606; 10,363,063; 10,588,687; 10,631,915; 10,639,098; and 10,639,101; and U.S. Patent Application Publications Nos. 2014/0066917; 2014/081260; 2014/0121658; 2021/0121224; 2021/0236191; 2022/0202484; 2022/0202485; and 2022/0226039, all of which are incorporated herein by reference in their entireties.

Basivertebral nerve ablation (BVN) can be used to, for example, treat discogenic back pain or other conditions. The basivertebral nerve is ablated using RF energy. Typically, the root or central confluence of the major basivertebral nerve intravertebral body branches is located in the near center of the patient's vertebral body (for example, approximately 50%/50% cranial-to-caudal, 50%/50% left-to-right, and 60%-75%/25%-40% anterior-to-posterior.) In at least some embodiments, to access this ablation target a tunnel is created through the vertebral bone and then an electrode is inserted into the vertebral bone for ablation. In at least some embodiments, to form the tunnel the clinician uses a tool to traverse the pedicle of the vertebrae (either left or right side) and then make a turn towards midline. Instead of transpedicular, an extrapedicular approach can be used.

In at least some embodiments, an access tool is used to create a straight tunnel through the pedicle to the vertebral body. Instead of transpedicular, an extrapedicular approach can be used. A tamp tool is then used to create a curved tunnel in the bone. The tamp tools described herein can be used to create a curved tunnel within a hard tough media such as bone. In at least some embodiments, the tamp tool is capable of creating a curved tunnel with enough curve for the various anatomies presented by patient diversity (for example, differences in age, gender, size, or the like or the presence of a disease or disorder, such as scoliosis, which may alter bone shape, density, homogeneity, vertebral form, or the like.) In at least some embodiments, the tamp tool is capable of creating a curved tunnel throughout a range of vertebral levels (for example, at least L3 through S1).

In at least some embodiments, the tamp of the tamp tool is straightened to travel down the pedicle. In at least some embodiments, when the tamp enters the vertebral body a portion of the tamp curves. For example, a portion of the tamp curves toward the midline. In at least some embodiments, the tamp tool is sufficiently durable to survive the tunneling action performed by a clinician with a mallet and is also sufficiently flexible to turn.

In at least some embodiments, the tamp tool retains the ability to carve a curved tunnel throughout multiple uses. Many ablation procedures involve ablating 2, 3, 4, or more vertebral levels. Moreover, on occasion tunneling is unsuccessful due to bone deformities, anatomy, or other factors and the tamp tool may be used multiple times at a single vertebral level.

Figures 2, 3:
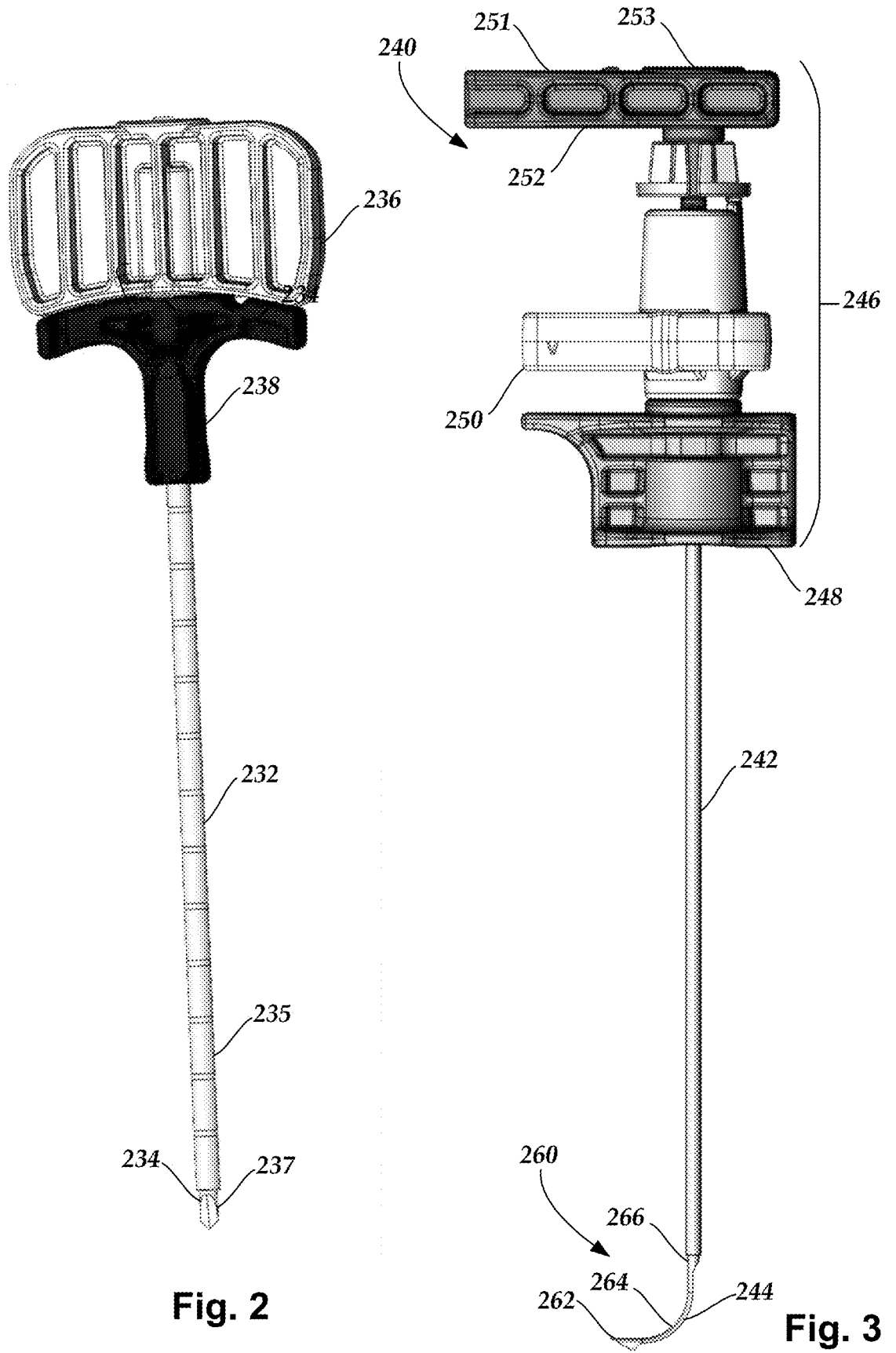
FIG. 2 is a schematic perspective view of one embodiment of an access tool and stylet.
FIG. 3 is a schematic side view of one embodiment of a tamp tool.

FIG. 2 illustrates one embodiment of an access tool 232 with a stylet 234 inserted into an open lumen of an access tool cannula 235 of the access tool leaving a stylet handle 236 of the stylet outside of the access tool and adjacent to an access tool cannula handle 238 of the access tool. A tip 237 of the stylet 234 can have any suitable shape including, but not limited to, bevel, diamond, trocar, or the like.

FIG. 3 illustrates one embodiment of a tamp tool 240 that includes a tamp cannula 242 fits into the open lumen of the access tool cannula 235, a tamp 244 that extends through the tamp cannula and is retractable into, and extendable out of, a distal end of the tamp cannula, and a tool hub 246 attached to a proximal end of the tamp cannula. The tamp cannula 242 and access tool cannula 235 are straight and do not curve. In particular, the distal end portions of the tamp cannula 242 and access tool cannula 235 do not curve.

Figure 5:
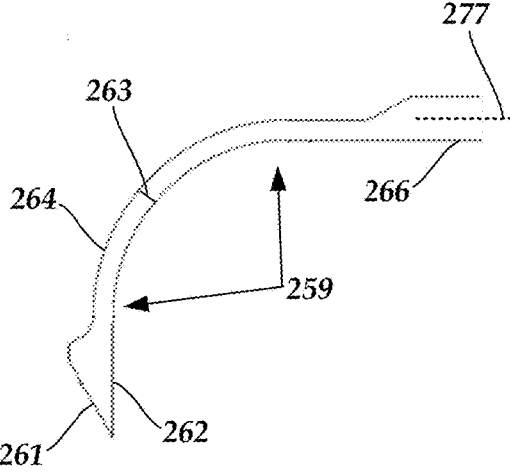
FIG. 5 is a schematic side view of a distal portion of a tamp of a tamp tool.

The distal portion 260 of the tamp 244 includes a tip 262, a curvable portion 264, and a shaft 266 (see, also, FIG. 5.) In at least some embodiments, the tamp 244, or at least the curvable portion 264 of the tamp, is constructed of nitinol, spring steel, or any other suitable flexible metal or other material. In at least some embodiments, the curvable portion 264 is biased to curve unless a force is applied to straighten the curvable portion. In at least some embodiments, the curvable portion 264 of the tamp 244 can be bent and held by a jig and then heat set in an oven (for example, heat set at 520° C. (or any other suitable temperature) for 8 minutes in a bath of heated salt) to bias the curvable portion 264 to curve. In at least some embodiments, a polymeric material can be overmolded, heat shrunk, or otherwise disposed over the curvable portion 264 to provide consistent cross-sectional dimension(s).

Figure 4A:
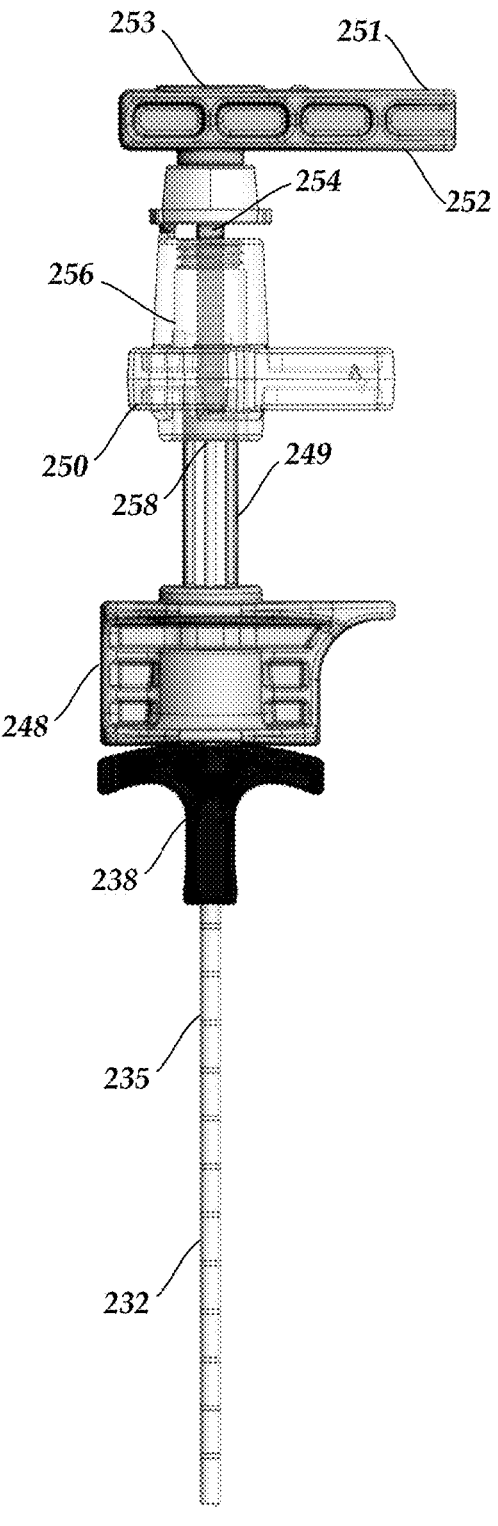
FIG. 4A is a schematic side view of the tamp tool of FIG. 3 coupled to the access tool of FIG. 2 with a tamp of the tamp tool retracted.

FIG. 3 illustrates one embodiment of one type of tool hub 246 that includes a stationary cannula attachment 248, a rotatable collar 250, and a movable head 252. In at least some embodiments, the tamp cannula 242 is attached to the stationary cannula attachment 248 of the tool hub 246. As illustrated in FIG. 4A, the movable head optionally includes an impact element 253 attached to a threaded post 254 and optionally includes a grip 251. The collar 250 includes a lumen 256 with a threaded portion that interacts with the threaded post 254 and the stationary cannula attachment 248 comprises a shaft 249 that fits within the lumen 256 of the collar. The threaded post 254 is attached to a proximal portion 258 of the tamp 244.

In operation, the stylet 234 is inserted into the access tool 232, as illustrated in FIG. 2, and then this combination is inserted into either the left or right pedicle. After passing through the pedicle, the stylet 234 is removed. Instead of transpedicular, an extrapedicular approach can be used with the access tool 232, where the stylet 234 is removed after entry into the vertebra.

The tamp tool 240 is then obtained with the tamp 244 retracted into the tamp cannula 242. The tamp cannula 242 of the tamp tool 240 is inserted into the access tool cannula 235 of the access tool 232, as illustrated in FIG. 4A.

In at least some embodiments, the tamp cannula 242 and the access tool cannula 235 of the access tool 232 are arranged so that the distal ends of the tamp cannula 242 and the access tool cannula 235 terminate at or near the same position in the vertebra when the tamp cannula 242 is fully inserted into the access tool cannula 235. In at least some embodiments, the tamp cannula 242 and the access tool cannula 235 of the access tool 232 are arranged so that the distal end of the tamp cannula 242 extends out of the distal end of the access tool cannula 235 when the tamp cannula 242 is fully inserted into the access tool cannula 235.

Figures 4B, 4C:
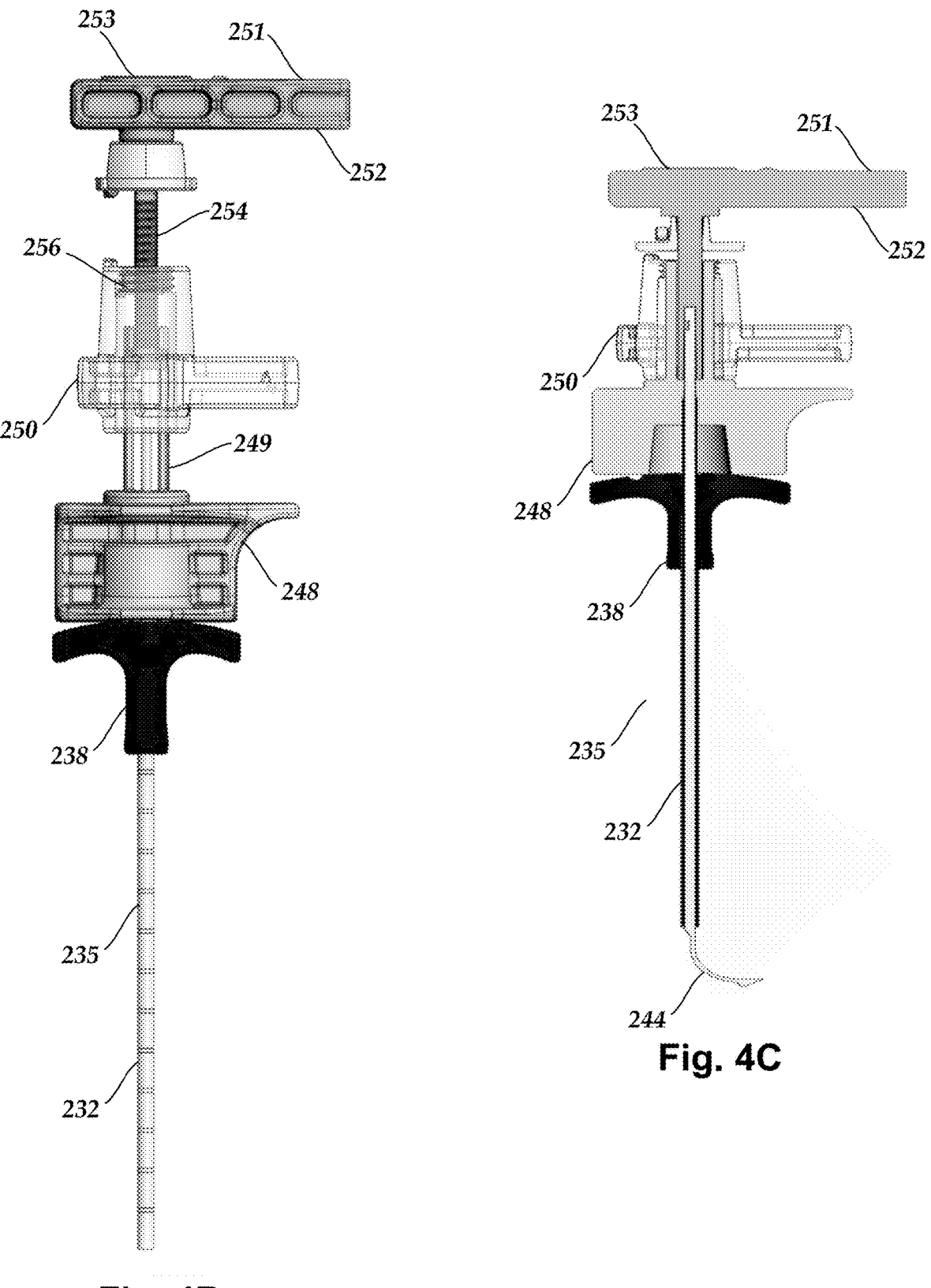
FIG. 4B is a schematic side view of the tamp tool of FIG. 3 coupled to the access tool of FIG. 2 with a tamp of the tamp tool retracted prior to extending the tamp.
FIG. 4C is a schematic cross-sectional side view of the tamp tool of FIG. 3 coupled to the access tool of FIG. 2 with the tamp of the tamp tool extended.

The collar 250 is rotated to retract the collar away from the stationary cannula attachment 248, as illustrated in FIG. 4B. The movable head 252 is then hammered (with a hammer or mallet) or otherwise operated to push the movable head 252 and collar 250 toward the stationary cannula attachment 248, as illustrated in FIG. 4C. The combination of the movable head 252 and the collar 250 slide along the shaft 249 of the stationary cannula attachment 248. In at least some embodiments, the shaft 249 or other part of the stationary cannula attachment 248 acts as a stop when the collar 250 is pushed against the stationary cannula attachment 248, as illustrated in FIG. 4C.

Pushing the movable head 252 and the collar 250 towards the stationary cannula attachment 248 extends the tamp 244 out of the tamp cannula 242, as illustrated in FIG. 3, to form the tunnel into the vertebral bone. As the tamp 244 extends out of the tamp cannula, the curvable portion 264 of the tamp 244 curves to form a curved tunnel in the vertebra.

Figure 4D:
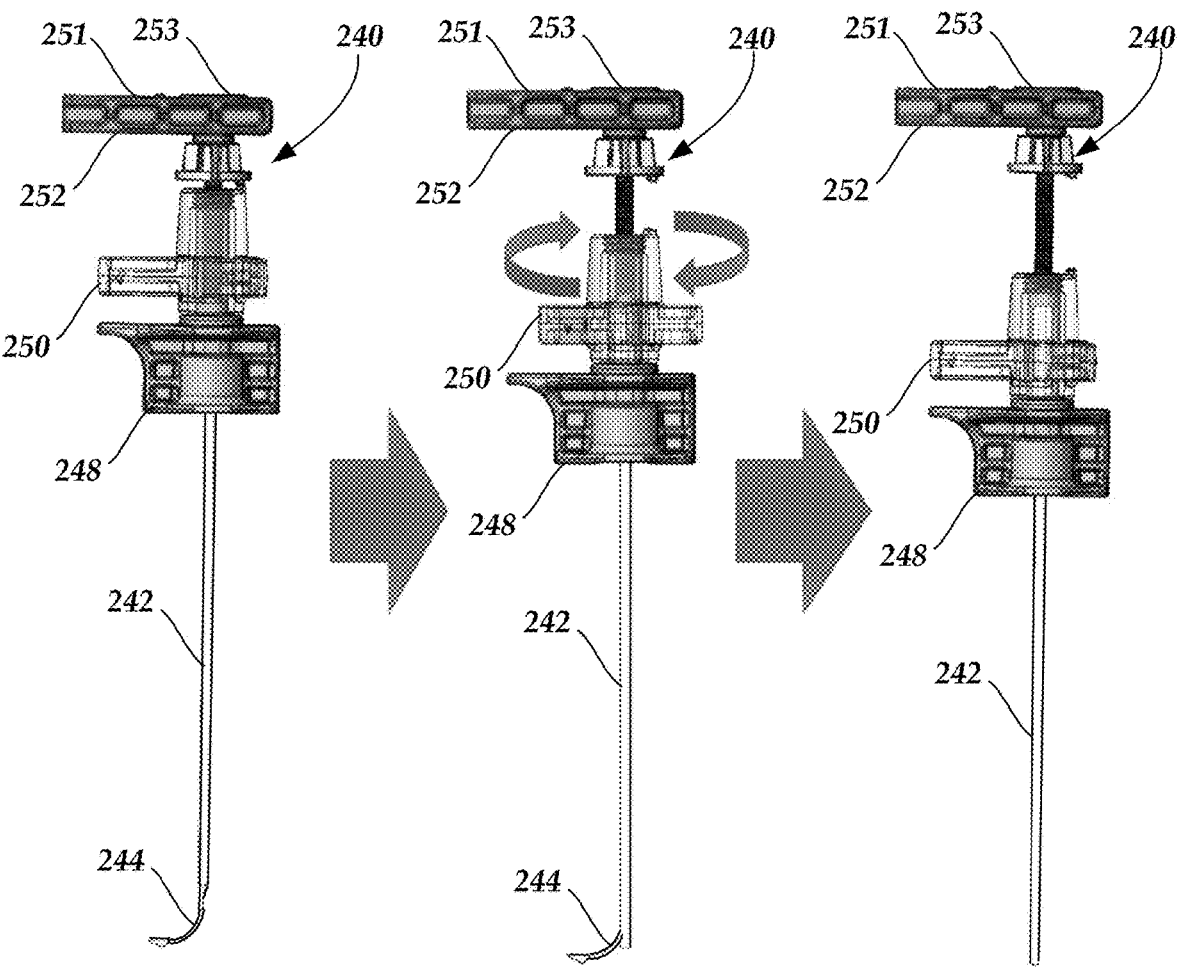
FIG. 4D is three schematic side views of the tamp tool of FIG. 3 illustrating the retraction of the tamp into a tamp cannula of the tamp tool.

After the tunnel is created, the collar 250 is rotated, while maintaining contact with the stationary cannula attachment 248, so that the movable head 252 moves away from the collar 250 as the collar 250 rotates and the threaded post 254 translates upward, as illustrated in FIG. 4D. This retracts the tamp 244 back into the tamp cannula 242. The retraction of the tamp 244 straightens the tamp within the straight tamp cannula 242. The tamp tool 240 is then removed from the access tool 232. In at least some embodiments, the access tool 232 may also be used for the cannula 106 or RF electrode(s) 104 (or both) of the RF ablation system 100 (see, FIG. 1.) In at least some embodiments, the tamp 244 can include one or more electrodes, for example, on or near a distal tip 262 (FIG. 5) and can act as a monopolar or bipolar RF electrode to perform RF ablation. In at least some embodiments, the tamp cannula 242 can act as a return electrode.

In at least some embodiments, the tamp tool 240 can include a stop that prevents the tamp 244 from being drawn too far into the tamp cannula 242. This may prevent or hinder the tip 262 (FIG. 5) of the tamp 244 from digging into the interior wall of the tamp cannula 242.

Figures 4E, 6A, 6B, 6C, 6D, 6E, 6F:
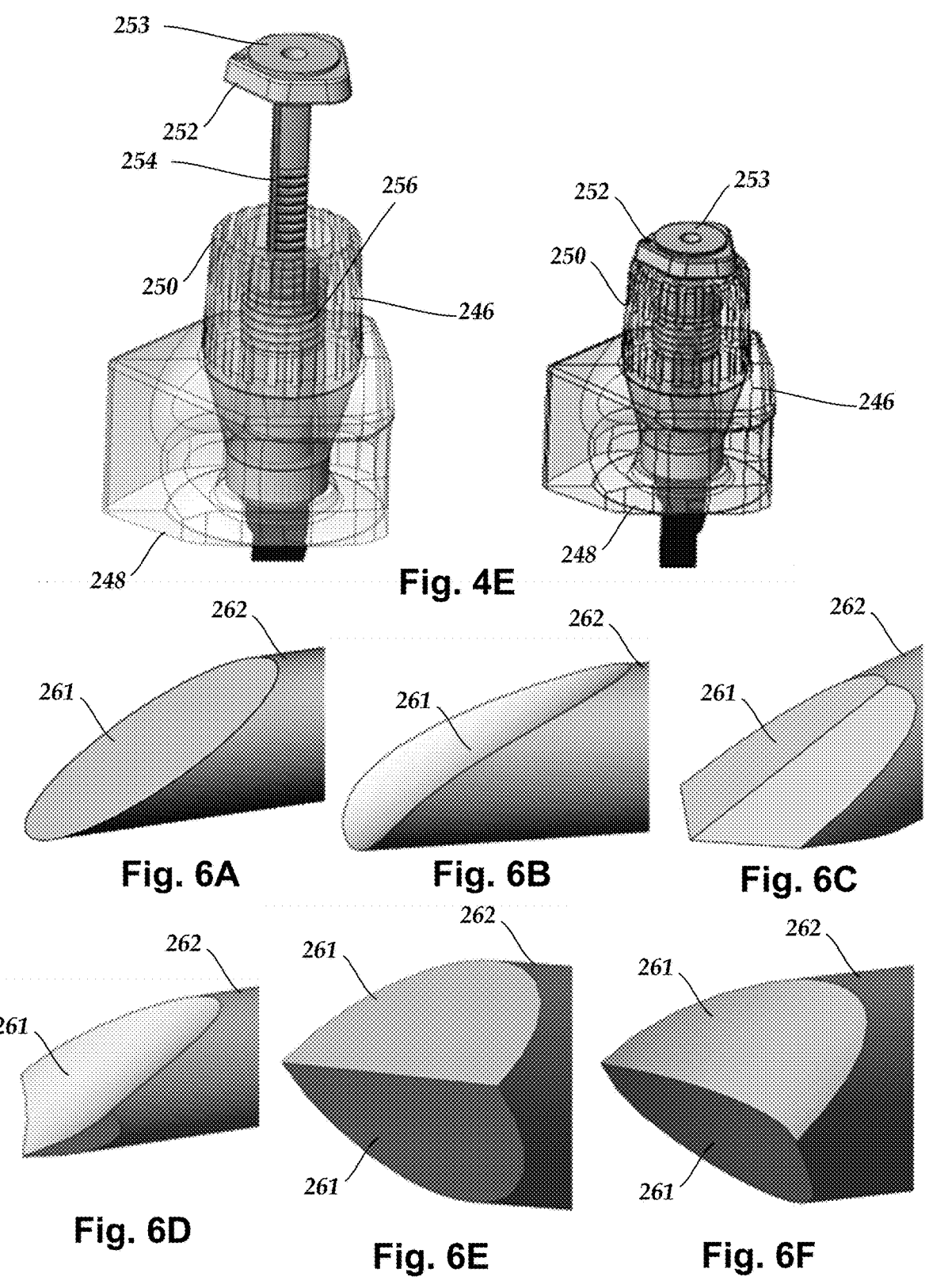
FIG. 4E presents two schematic perspective views of a tool hub of another embodiment of a tamp tool with the tamp in the retracted position (left) or extended position (right)
FIGS. 6A to 6G are perspective views of different embodiments of a tip of a tamp of a tamp tool.

FIG. 4E illustrates another embodiment of a tool hub 246 including a movable head 252 with an impact element 253 and a threaded post 254, a stationary cannula attachment 248, and a rotatable collar 250 with a lumen 256 having a threaded portion. In at least some embodiments, as illustrated in FIG. 4E, the rotatable collar 250 may not move up or down relative to the stationary cannula attachment 248. In FIG. 4E, the left illustration is the tool hub 246 with the tamp retracted into the tamp cannula and the right illustration is the tool hub with the tamp extended out of the tamp cannula.

Figure 4F:
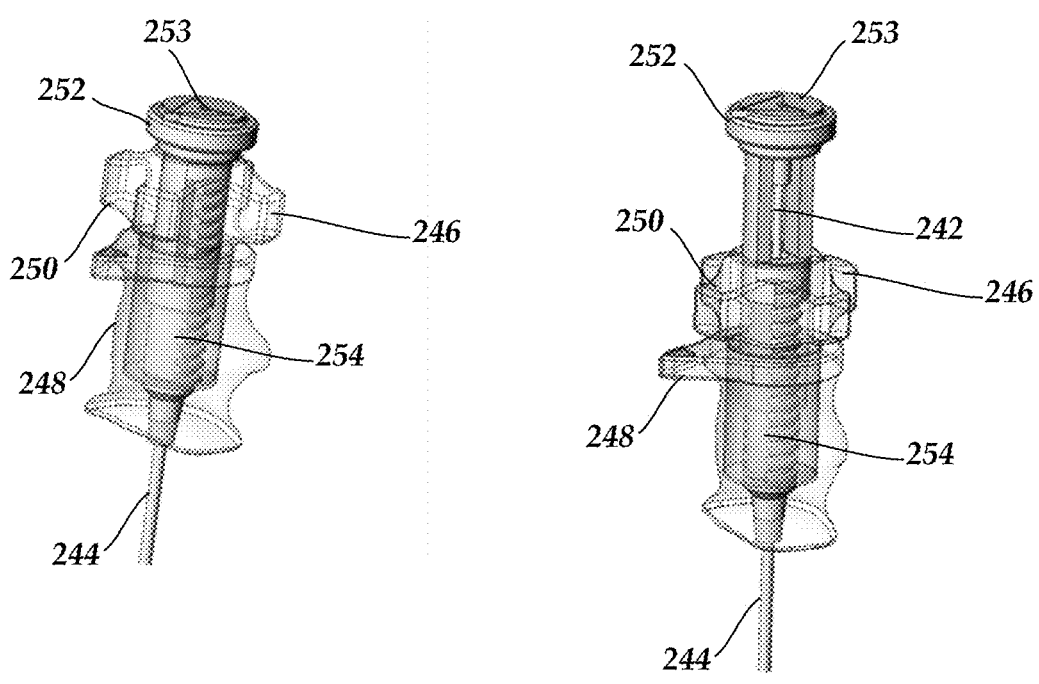
FIG. 4F presents two schematic perspective views of a tool hub of a further embodiment of a tamp tool with the tamp in the retracted position (left) or extended position (right)

FIG. 4F illustrates a further embodiment of a tool hub 246 including a movable head 252 with an optional impact element 253, a stationary cannula attachment 248 with a threaded post 254, and a rotatable collar 250 that functions similar to the tool hub 246 illustrated in FIG. 4E. In at least some embodiments, as illustrated in FIG. 4F, the rotatable collar 250 does not move up or down relative to the stationary cannula attachment 248. In FIG. 4F, the left illustration is the tool hub 246 with the tamp retracted into the tamp cannula and the right illustration is the tool hub with the tamp extended out of the tamp cannula.

Figure 4G:
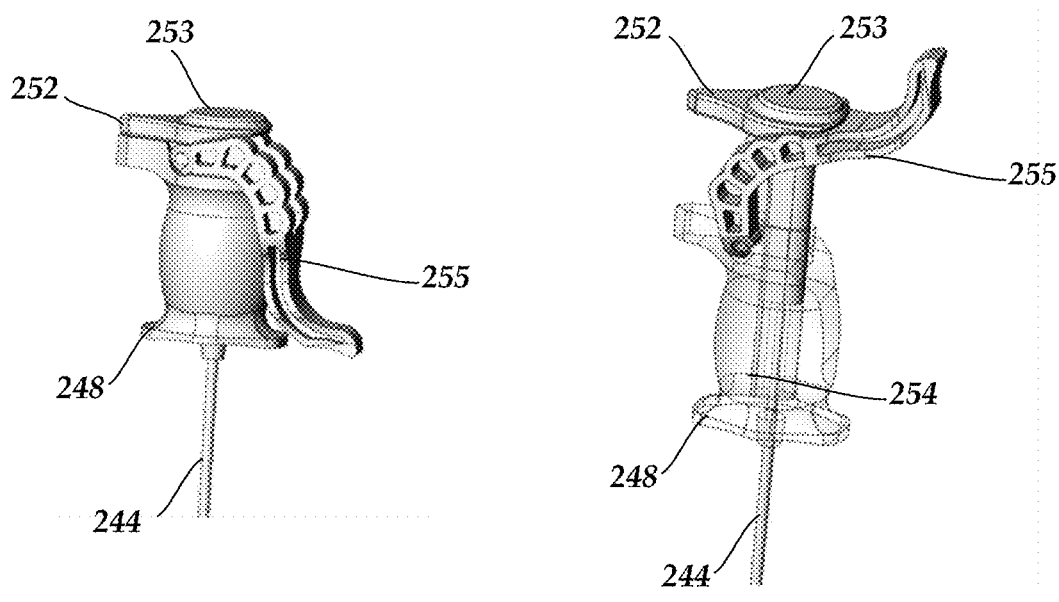
FIG. 4G presents two schematic perspective views of a tool hub of yet another embodiment of a tamp tool with the tamp in the retracted position (left) or extended position (right)

FIG. 4G illustrates yet another embodiment of a tool hub 246 including a movable head 252 with an optional impact element 253, a stationary cannula attachment 248, and a cam handle 255. In at least some embodiments, as illustrated in FIG. 4G, the rotatable handle 255 is operated to translate the movable head 252 (which is attached to the tamp) up or down. In FIG. 4G, the left illustration is the tool hub 246 with the tamp retracted into the tamp cannula and the right illustration is the tool hub with the tamp extended out of the tamp cannula.

Although the examples described herein include a tamp cannula 242, it will be understood that in other embodiments, the tamp cannula is not present and the access tool cannula 235 can be used, instead, for any of the functions described herein for the tamp cannula. For example, the access tool cannula 235 can straighten the tamp 244 as the tamp is received in the access tool cannula.

Figures 6G, 7A, 7B:
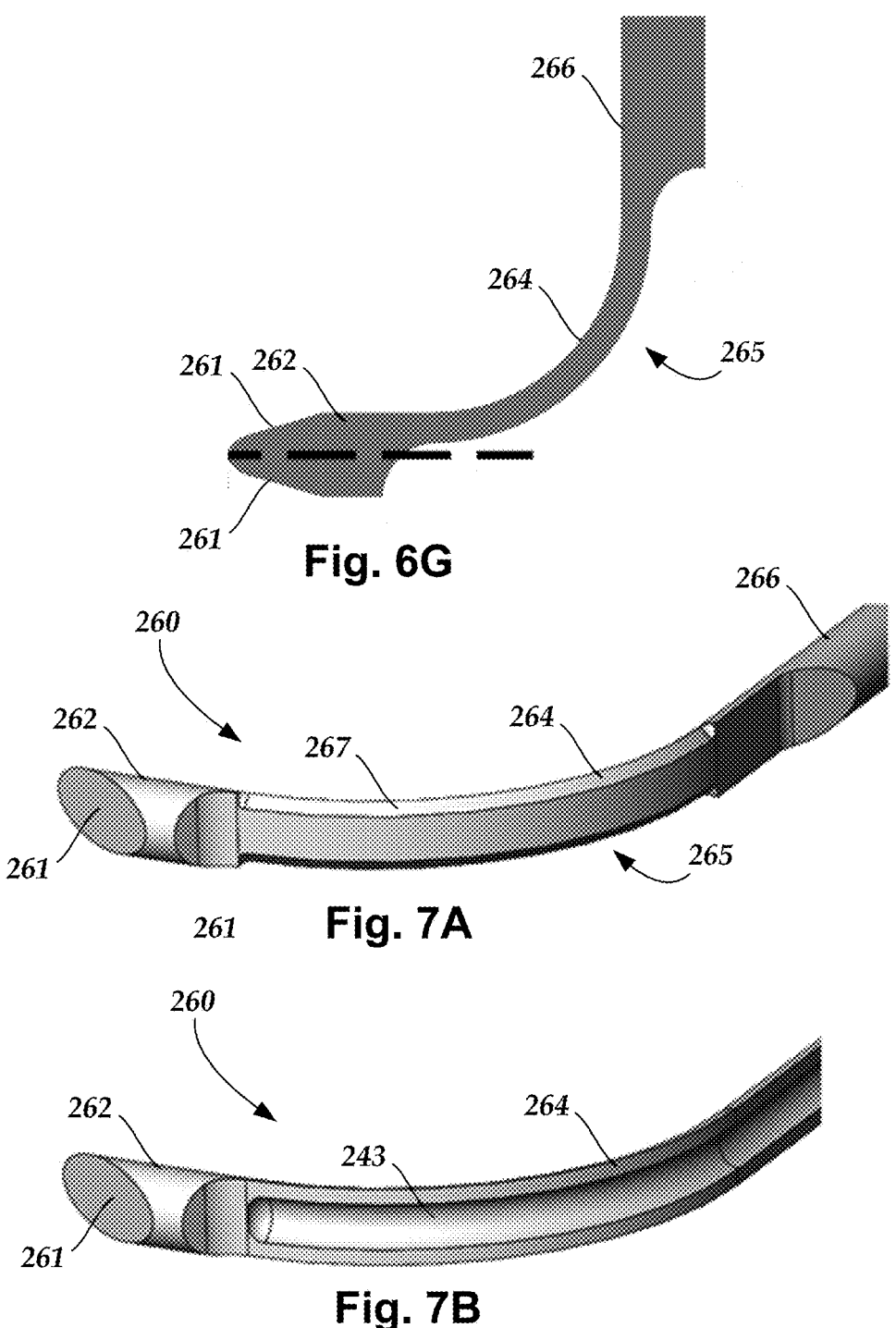
FIG. 7A is a schematic perspective view of a distal portion of one embodiment of a tamp.
FIG. 7B is a schematic perspective view of a distal portion of another embodiment of a tamp with a relieve channel.

Turning to FIG. 5 and the tamp 244, in at least some embodiments, the tip 262 of the tamp is pointed. In at least some embodiments, the tip 262 includes a slanted face 261 in the direction of the bend 259 of the curvable portion 264, as illustrated in FIG. 5, to aid in curving. Examples of other slanted faces 261 of the tip 262 are illustrated in FIG. 6A to 6G and include a beveled tip (FIG. 6A), a curved tip (FIG. 6B, which may facilitate a sharp point), a multi-faced tip (FIG. 6C), a splayed tip (FIG. 6D), a double wedge tip (FIG. 6E), a curved double wedge tip (FIG. 6F), or a blunted tip (FIG. 6G). It will be recognized that any other suitable tip 262 can also be used. Similar tips can be used for the tip 237 of the stylet 234 of FIG. 2.

In at least some embodiments, the curvable portion 264 has a smaller thickness 263 in the plane of the bend as compared to the portions of the tip 262 and the shaft 266 immediately adjacent to the curvable portion, as illustrated in FIG. 5. In at least some embodiments, the lateral width 263 is at least 0.042 inches (or approximately 1 mm). In at least some embodiments, the curvable portion 264 has a smaller thickness 263 in the plane of the bend than a width of the curvable portion perpendicular to the plane of the bend.

In at least some embodiments, the curvable portion 264, when fully extended out of the tamp cannula 242, bends at an angle of at least 60, 65, 70, 75, 80, 85, or 90 degrees. In at least some embodiments, the curvable portion 264, when fully extended out of the tamp cannula 242, bends at an angle of no more than 100 or 90 degrees.

In at least some embodiments, a smaller or larger length of the curvable portion 264 can result in a smaller or larger radius of curvature. In at least some embodiments, a smaller radius of curvature may be desirable for a vertebral level with smaller or more laterally oriented pedicle or a smaller vertebral body. In at least some embodiments, a larger radius may be desirable for a vertebral level with a larger or more medially oriented pedicle or a larger vertebral body.

In at least some embodiments, at least a portion of edges 267 of the curvable portion 264 are relieved inwardly toward a center of the curvable portion 264 relative to adjacent portions of the tip 262 and the shaft 266, as illustrated in FIG. 7A. In at least some embodiments, the edges 267 of the curvable portion 264 are relieved. This may facilitate retraction of the tamp 244 back into the tamp cannula 242.

In at least some embodiments, the distal portion 260 of the tamp 244 defines a cutout 265 between the tip 262 and the shaft 266. The cutout 265 can be described as a portion of the tamp 264 that is removed or absent when considered relative to the adjacent parts of the tip 262 and the shaft 266. This results in the curvable portion 264 having a thinner part of the tamp 244 as compared to the adjacent parts of the tip 262 and the shaft 266. In at least some embodiments, the curvable portion 264 is defined by the cutout 265 which facilitates curving. In at least some embodiments, the curvable portion 264 curves away from the cutout 265, as illustrated in FIGS. 5 and 7A.

In at least some embodiments, the cross-section of the curvable portion 264 can have a D-shape or be roughly D-shaped. In at least some embodiments, the straight portion of the D-shape is defined by the cutout 265. In at least some other embodiments, the cross-section of the curvable portion 264 can be circular, oval, square, rectangular, tetrahedral, hexagonal, octagonal, or any other suitable shape. In at least some embodiments, a circular or other shape with similar dimensions in multiple directions (e.g., square, hexagonal, octagonal or the like) may facilitate actively steering the bending of the curvable portion 264 in different directions. A rectangular or oval cross-section may result in preferential bending directions.

In at least some embodiments, the curvable portion 264 includes a relieved channel 243 extending along at least a portion of the curvable portion 264, as illustrated in FIG. 7B. The lateral cross-sectional contour of the relieved channel 264 can be curved, as illustrated in FIG. 7B, square, triangular, pentagonal, hexagonal, octagonal, or any other suitable regular or irregular shape.

Figures 8A, 8B, 8C, 8D, 8E:
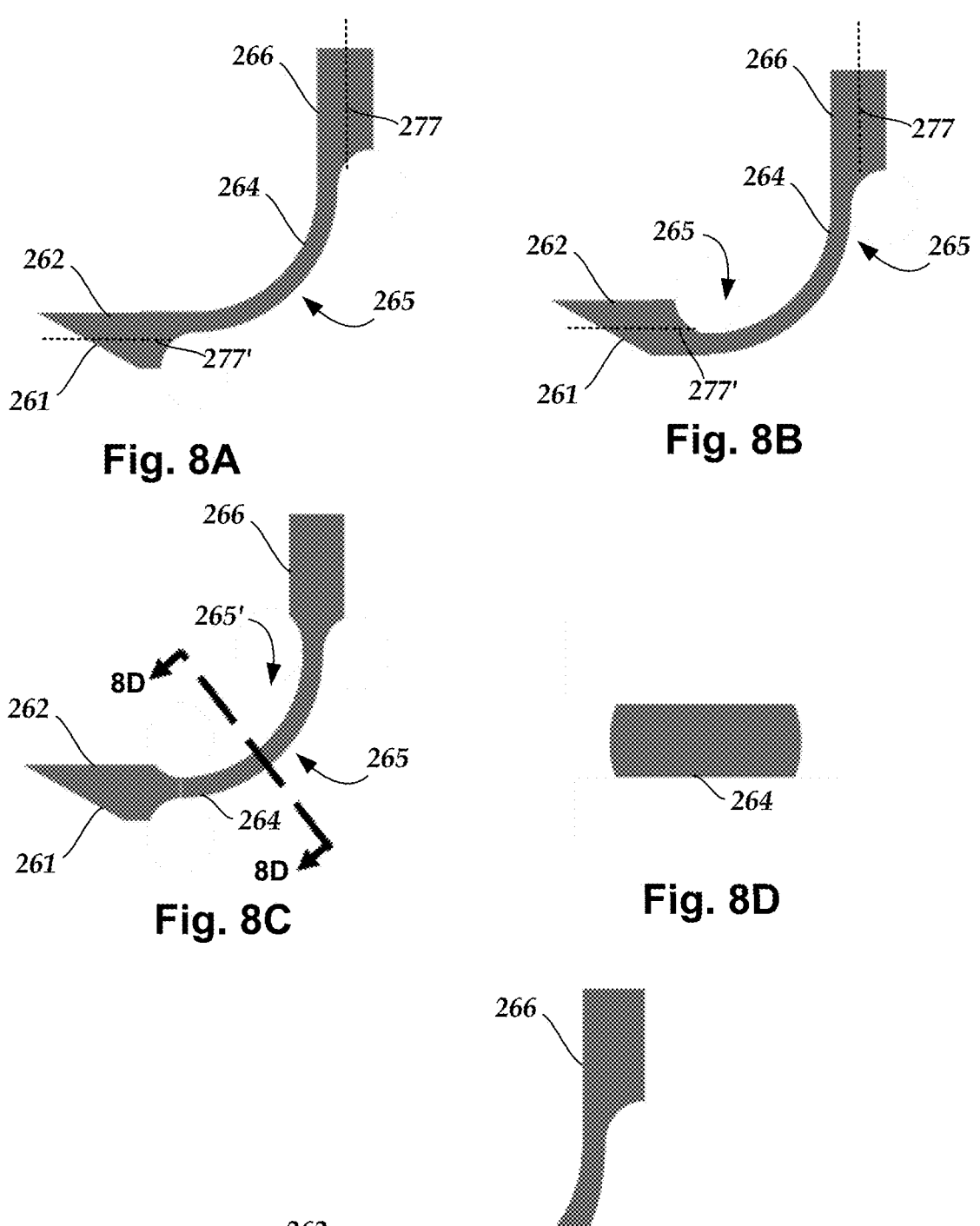
FIG. 8A is a schematic side view of a distal portion of a first embodiment of a tamp with a cutout portion defining a curvable region of the tamp.
FIG. 8B is a schematic side view of a distal portion of a second embodiment of a tamp with a cutout portion defining a curvable region of the tamp where the curvable region is offset in one direction from a central axis of a shaft of the tamp and offset in another direction from a central axis of a tip of the tamp.
FIG. 8C is a schematic side view of a distal portion of a third embodiment of a tamp with two opposing cutout portions defining a curvable region of the tamp.
FIG. 8D is a cross-sectional view of the curvable region of the tamp of FIG. 8C.
FIG. 8E is a schematic side view of a distal portion of a fourth embodiment of a tamp with a variable thickness of the curvable region of the tamp.

In at least some embodiments, the curvable portion 264 is offset relative to the center axis 277 of the adjacent part of the shaft 266, as illustrated in FIGS. 5 and 8A. In at least some embodiments, the curvable portion 264 is offset relative to the center axis 277' of the adjacent part of the tip 262, as illustrated in FIG. 8A. In at least some embodiments, the curvable portion 264 is offset toward the inside of the bend, as illustrated in FIGS. 5 and 8A. In at least some embodiments, this direction of bending or curving has been found to create a smooth tunnel. It will be understood, however, that the curvable portion 264 can be designed to bend in the other direction so that the offset is toward the outside of the bend.

In at least some embodiments, the curvable portion 264 of the tamp 244 can be offset in one direction from the central axis of the shaft 266 and offset in the opposite direction from the tip 262, as illustrated in FIG. 8B. In at least some embodiments, such an arrangement may reduce strain on the curvable portion 264.

In at least some embodiments, the tamp 244 includes a supplemental cutout 265' opposite the cutout 265, as illustrated in FIG. 8C. In at least some embodiments, the curvable portion 264 remains offset relative to the center axis 277 of the adjacent part of the shaft 266 or may be centered relative to the center axis of the adjacent part of the shaft. FIG. 8D illustrates one embodiment of a cross-section for the curvable portion 264 defined by a cutout 265 and supplemental cutout 265'.

In at least some embodiments, the curvable portion 264 has a uniform thickness along a length of the curvable portion 264 (optionally, except for relatively short region(s) adjacent the tip 262 or the shaft 266 or both the tip and shaft.) In at least some embodiments, the curvable portion 264 has a variable thickness along the length of the curvable region, as illustrated in FIG. 8E. In FIG. 8E, the thickness of the curvable portion 264 decreases from the distal end to the proximal end of the curvable portion. Such an arrangement may facilitate more aggressive curving as the tamp 244 exits the tamp cannula 242 with increased flexibility as the tamp continues to exit the tamp cannula. It will be recognized that other patterns of thickness variability can be used including, but not limited to, increasing thickness from the distal end to the proximal end or increasing thickness followed by decreasing thickness (or vice versa) along the length of the tamp. These variations in thickness can occur along the entire curvable portion 264 or along one or more parts of the curvable portion.

In at least some embodiments, the cutout 265 also defines at least one straight section 269, in addition to the curvable portion 264, as illustrated in FIG. 9A. In at least some embodiments, a straight section 269 may be disposed adjacent the shaft 266, as illustrated in FIG. 9A. In at least some embodiments, this positioning of a straight section 269 may provide strain relief for the tamp 244, particularly when the tamp 244 is positioned or retracted into the tamp cannula 242.

In at least some embodiments, a straight section 269' may be disposed adjacent the tip 262, as illustrated in FIG. 9B. In at least some embodiments, this positioning of a straight section 269' may facilitate clearing the tunnel formed by the tamp 244 as the tamp is retracted into the tamp cannula 242. In at least some embodiments, this positioning of a straight section 269' may facilitate forming a tunnel with an elliptical cross-section.

Other arrangements for a curvable portion 264 can be used. For example, the curvable portion 264 can be made of a tube of curvable material, such as nitinol, as illustrated in FIGS. 10A and 10B. In at least some embodiments, the curvable portion 264 is defined, at least in part, by multiple cutout teeth 271, as illustrated in FIG. 10C, or a set of microcuts 273, as illustrated in FIG. 10D.

Figures 10E, 10F, 11A, 11B, 11C:
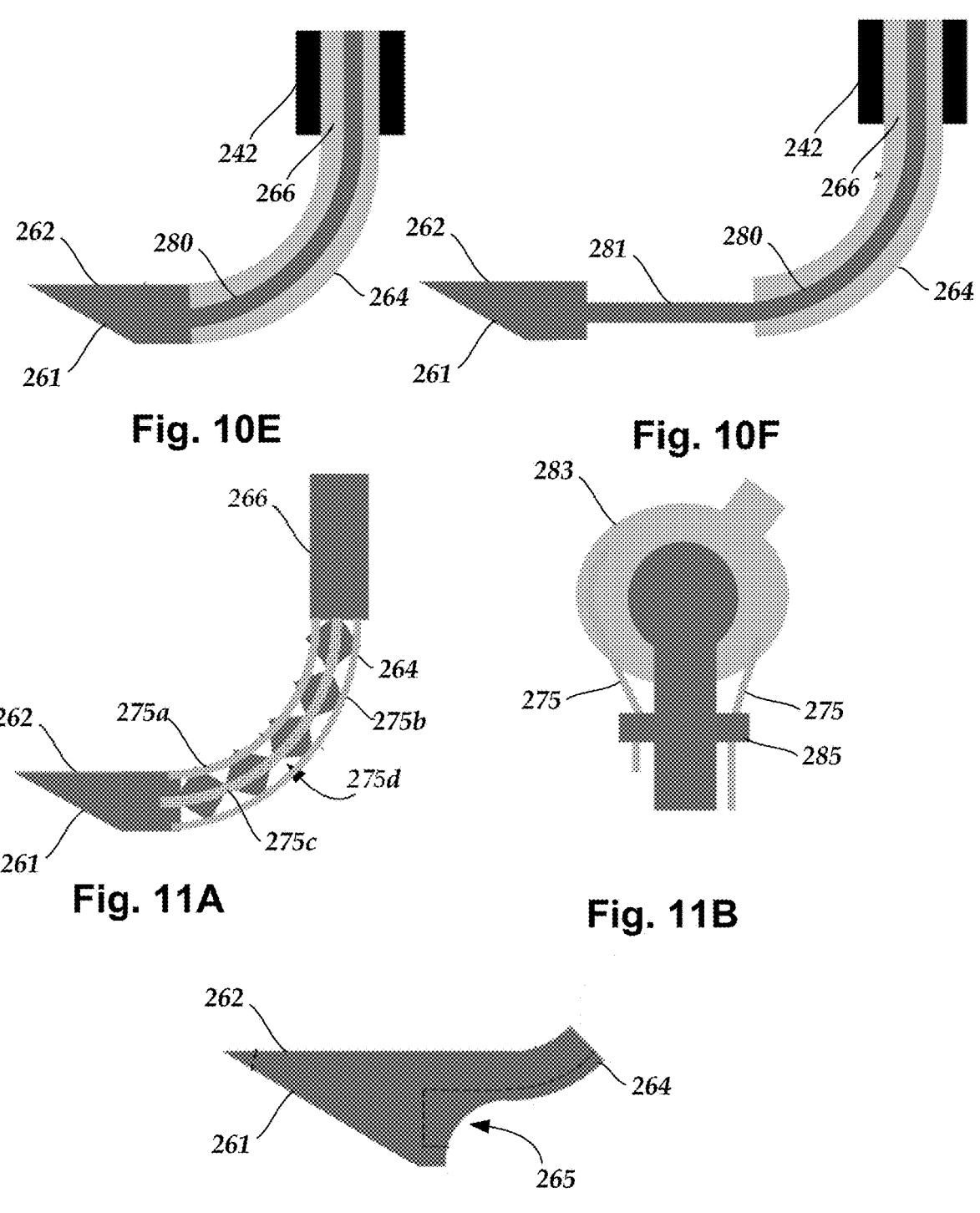
FIG. 10E is a schematic side view of a distal portion of a tenth embodiment of a tamp with a curvable region of the tamp formed using a curvable tube and a stylet extending through the curvable tube and having a tip of the tamp at the distal end of the stylet.
FIG. 10F illustrates the distal portion of the tamp of FIG. 10E with the stylet extending further out of the curvable tube.
FIG. 11A is a schematic side view of a distal portion of an eleventh embodiment of a tamp with a curvable region and with pull wires attached to the tip for guiding the tamp.
FIG. 11B is schematic side view of one embodiment of a handle for operating the pull wires.
FIG. 11C is a schematic side view of a tip of a twelfth embodiment of a tamp having an opening in the tamp for receiving bone fragments or particulates.

Another embodiment of a tamp 244 includes a curvable portion 264 that is made of a curvable tube (such as a nitinol tube) and a stylet 280 that extends through the curvable portion 264 and forms the tip 262, as illustrated in FIG. 10E. In at least some embodiments, the stylet 280 can also be extended further out of the curvable portion 264, as illustrated in FIG. 10F. In at least some embodiments, the portion 281 of the stylet 280 that extends out of the curvable portion is straight, as illustrated in FIG. 10F.

In at least some embodiments, the tamp 244 can include one or more pull-wires 275, as illustrated in FIG. 11A. In at least some embodiments, each pull wire 275 is attached to the tip 262 (or the curvable portion 264) and extends through the shaft 266 (or outside the shaft but within the tamp cannula 242) to the tool hub 246. The pull wire(s) 275 can be used to steer the tip 262 or curvable portion 264. A tamp 244 may include one or more of the pull wires 275*a*, 275*b*, 275*c*, 275*d* illustrated in FIG. 11A.

As an example, in FIG. 11A, a tamp 244 can include one or both of pull wires 275*a*, 275*b* which can be used to alter the amount of bending of the curvable portion 264. Pulling pull wire 275*a* may increase bending. Pulling pull wire 275*b* may decrease bending. As another example, in FIG. 11A, a tamp 244 can include one or both of pull wires 275*c*, 275*d* which can be used to alter the lateral direction (lateral relative to the direction of bending) of the curvable portion 264. FIG. 11B illustrates one embodiment of a handle 283 that is rotatable relative to a fixed element 285 and is attached to two pull wires 275 (for example, pull wires 275*a*, 275*b* or pull wires 275*c*, 275*d*) for operating the pull wires. In at least some embodiments, the handle 283 and fixed element 285 can be part of a tool hub (or adjacent to a tool hub).

In at least some embodiments, the tamp 244 can include an opening 265 in the proximal end of the tip 262, as illustrated in FIG. 11C. As the tamp 244 is retracted into the tamp cannula 242, bone fragments or other particles can be gathered into the opening 265 for at least partially clearing the tunnel created by the tamp.

Figures 12A, 12B, 12C, 12D:
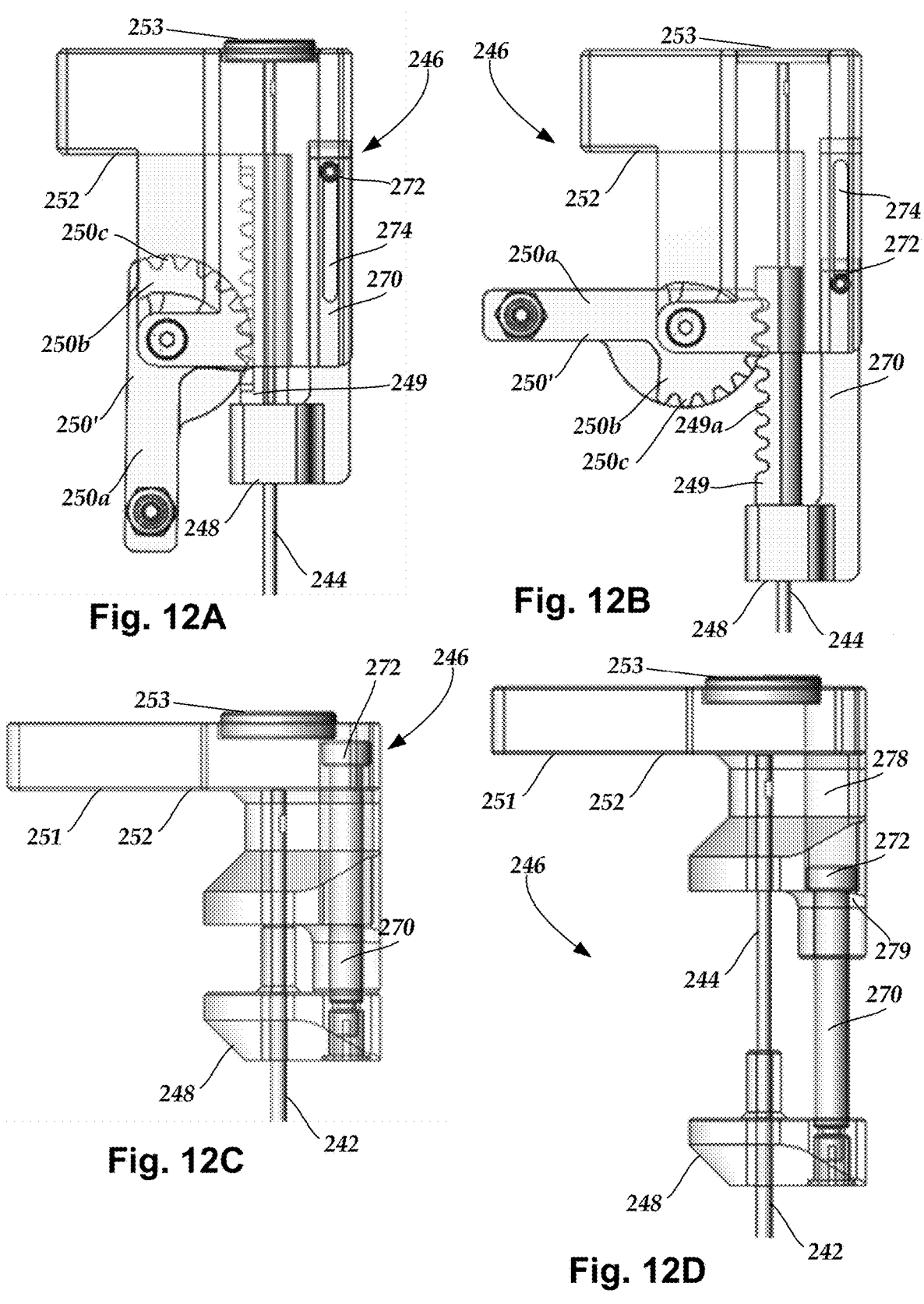
FIGS. 12A and 12B are schematic side view of another embodiment of a tool hub utilizing a rack and pinion arrangement for moving between an extended tamp (FIG. 12A) to a retracted tamp (FIG. 12B)
FIGS. 12C and 12D are schematic side view of a further embodiment of a tool hub utilizing another arrangement for moving between an extended tamp (FIG. 12C) to a retracted tamp (FIG. 12D)

Other arrangements of a tool hub 246 can be used. For example, FIGS. 12A and 12B illustrate a tool hub 246 with a rack and pinion mechanism in the deployed (left) and retracted (right) states. The tool hub 246 of FIGS. 12A and 12B includes a movable head 252 with an impact elements 253, as well as a stationary cannula attachment 248 with a rack 249 (e.g., a shaft) have teeth 249*a*. The movable head 252 is attached to a proximal portion of the tamp 244. Instead of a collar, the tool hub 246 of FIGS. 12A and 12B has a pinion 250' with a handle 250*a* and a circular gear 250*b* with teeth 250*c* that engage the teeth 249*a* of the shaft 249. The pinion 250' is attached to the movable head 252 and operation of the pinion 250' can move the movable head 252 up to the retracted state (FIG. 12B) or down to the deployed state (FIG. 12A). In at least some embodiments, the pinion 250' disengages from the rack 249 as the tamp 244 is extended out of the tamp cannula 242.

In at least some embodiments, the stationary cannula attachment 248 of the tool hub 246 of FIGS. 12A and 12B includes a movement limiting shaft 270 with a stop 272, such as a pin, bar, or the like and the movable head 252 includes a track 274 along which the stop 272 moves. Movement of the movable head 252 away from the stationary cannula attachment 248 is limited by the track 274 and the stop 272. When the stop 272 reaches an end of the track 274, the movable head 252 can move no further from the stationary cannula attachment 248.

Another arrangement of a tool hub 246 is illustrated in FIGS. 12C and 12D in the deployed (left) and retracted (right) states. The tool hub 246 of FIGS. 12C and 12D includes a movable head 252 with an optional impact element 253 and a grip 251 (or handle), as well as a stationary cannula attachment 248. The movable head 252 is attached to a proximal portion of the tamp 244. In at least some embodiments, the stationary cannula attachment 248 of the tool hub 246 of FIGS. 12C and 12D includes a movement limiting shaft 270 with a stop 272, such as a pin, bar, or the like and the movable head 252 includes a lumen 278 along which the stop 272 moves. Movement of the movable head 252 away from the stationary cannula attachment 248 is limited by the stop 272. When the stop 272 reaches a stop portion 279 of the lumen 278, the movable head 252 can move no further from the stationary cannula attachment 248. A clinician can use the grip 251 of the movable head 252 to separate the movable head from the stationary cannula attachment.

Figure 13:
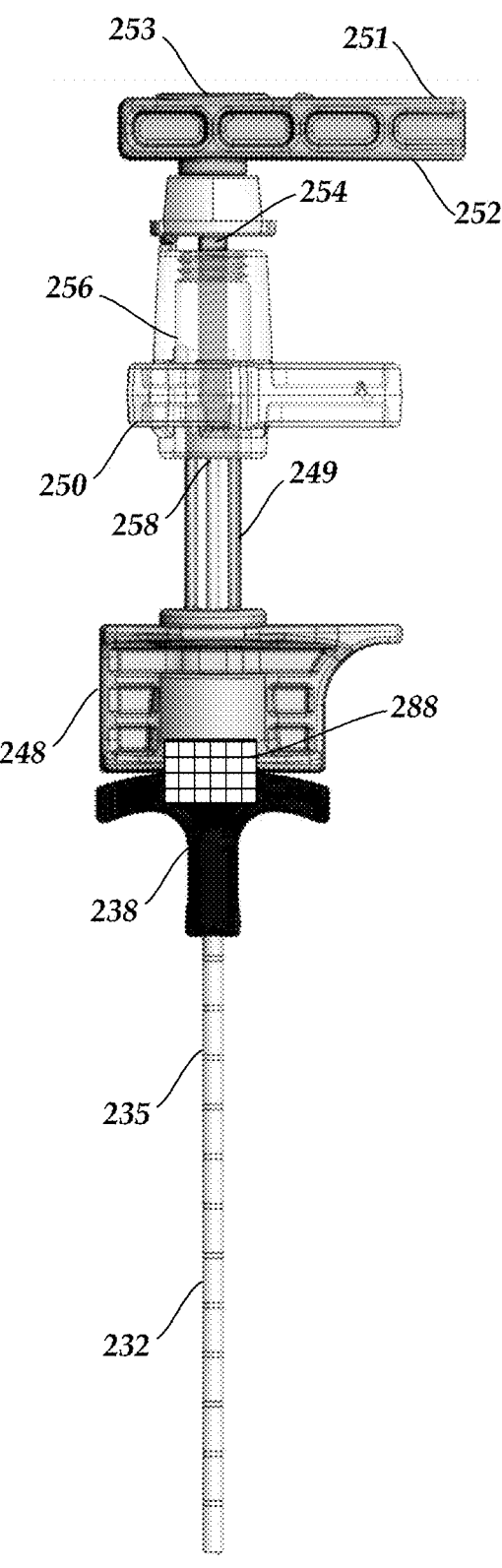
FIG. 13 is a schematic side view of the tamp tool of FIG. 3 coupled to the access tool of FIG. 2 with a locking mechanism for locking the tamp tool to the access tool.

In at least some embodiments, the tool hub 246 includes a locking mechanism 288 to lock the tool hub to the access tool 232, as illustrated in FIG. 13. For example, the stationary cannula attachment 248 of the tool hub 246 can be locked to the handle 238 of the access tool 232. Any suitable locking mechanism 288 including, for example, a detent panels and a groove on the handle 238, panels that create a friction attachment or other attachment, or the like or any combination thereof. In at least some embodiments, the locking mechanism 288 can prevent or reduce rotational or axial misalignment between the stationary cannula attachment 248 and the handle 238.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected by Letters Patent of the United States is:

1. A tool arrangement for forming a tunnel in a vertebra to perform nerve ablation, the tool arrangement comprising:
    a tamp comprising a distal end portion, a proximal end portion, and a shaft extending from the distal end portion to the proximal end portion, wherein the distal end portion comprises a tip configured for creating the tunnel in the vertebra and a curvable portion coupled to the tip and configured to direct the tip along a curved path within the vertebra;
    a first cannula comprising a cannula body defining a lumen through which the tamp is extendable, wherein the cannula body is straight along an entire length of the cannula body and the first cannula is configured to receive the curvable portion of the tamp and straighten the curvable portion when the curvable portion is received in the first cannula;
    a tool hub comprising a stationary cannula attachment coupled to the first cannula, a movable head coupled to the tamp and configured to move toward or away from the stationary cannula attachment to extend or retract, respectively, the curvable portion of the tamp from or into, respectively, the first cannula, and a rotatable collar disposed between the stationary cannula attachment and the movable head, wherein the stationary cannula attachment comprises an attachment shaft and the rotatable collar slides along the attachment shaft as the movable head moves toward the stationary cannula attachment to extend the curvable portion of the tamp out of the first cannula; and an access tool comprising an access tool handle and an access tool cannula, wherein the access tool cannula is straight along an entire length of the access tool cannula and the access tool is configured to receive the first cannula within the access tool cannula, wherein, when the first cannula is fully inserted into the access tool cannula, a distal end of the first cannula terminates at or near, or extends out of, a distal end of the access tool cannula.

2. The tool arrangement of claim 1, wherein the movable head comprises an impact element to receive impacts from a hammer or mallet.

3. The tool arrangement of claim 1, wherein the movable head comprises a threaded post.

4. The tool arrangement of claim 3, wherein the rotatable collar comprises a lumen with a threaded portion configured to receive and interact with the threaded post of the movable head.

5. The tool arrangement of claim 4, wherein rotating the rotatable collar moves the movable head away from or toward the stationary cannula attachment depending on a direction of rotation.

6. The tool arrangement of claim 1, wherein the curvable portion of the tamp is defined, relative to the shaft and the tip of the tamp, by a cutout and is offset relative to a central axis of at least one of the shaft or the tip of the tamp.

7. The tool arrangement of claim 6, wherein the curvable portion bends away from the cutout.

8. The tool arrangement of claim 1, wherein the curvable portion of the tamp defines a relieved channel along the curvable portion.

9. The tool arrangement of claim 1, further comprising at least two pull wires attached to the tip of the tamp to manually guide the tamp in forming the tunnel.

10. The tool arrangement of claim 6, wherein the curvable portion of the tamp is offset relative to the central axis of both the shaft and the tip of the tamp.

11. A method for forming a tunnel in a vertebra using a tool arrangement for forming a tunnel in a vertebra to perform nerve ablation, the tool arrangement comprising: a tamp comprising a distal end portion, a proximal end portion, and a shaft extending from the distal end portion to the proximal end portion, wherein the distal end portion comprises a tip configured for creating the tunnel in the vertebra and a curvable portion coupled to the tip and configured to direct the tip along a curved path within the vertebra; a first cannula comprising a cannula body defining a lumen through which the tamp is extendable, wherein the cannula body is straight along an entire length of the cannula body and the first cannula is configured to receive the curvable portion of the tamp and straighten the curvable portion when the curvable portion is received in the first cannula; a tool hub comprising a stationary cannula attachment coupled to the first cannula, a movable head coupled to the tamp and configured to move toward or away from the stationary cannula attachment to extend or retract, respectively, the curvable portion of the tamp from or into, respectively, the first cannula, and a rotatable collar disposed between the stationary cannula attachment and the movable head, wherein the stationary cannula attachment comprises an attachment shaft and the rotatable collar slides along the attachment shaft as the movable head moves toward the stationary cannula attachment to extend the curvable portion of the tamp out of the first cannula; and an access tool comprising an access tool handle and an access tool cannula, wherein the access tool cannula is straight along an entire length of the access tool cannula and the access tool is configured to receive the first cannula within the access tool cannula, wherein, when the first cannula is fully inserted into the access tool cannula, a distal end of the first cannula terminates at or near, or extends out of, a distal end of the access tool cannula, the method comprising:

inserting the access tool cannula of the access tool into the vertebra of a patient, wherein the access tool cannula is straight;

inserting the first cannula into the access tool cannula of the access tool, wherein the first cannula is straight;

inserting the tamp into the first cannula; and operating the tool hub to extend the distal end portion of the tamp out of a distal end of the first cannula to form the tunnel, wherein the curvable portion of the tamp is biased to curve when outside of the first cannula, wherein the curvable portion is straightened within the first cannula prior to extending out of the distal end of the first cannula.

12. The method of claim 11, wherein operating the tool hub comprises driving the movable head of the tool hub toward the stationary cannula attachment of the tool hub, wherein the tamp is coupled to the movable head.

13. The method of claim 11, further comprising after forming the tunnel, operating the tool hub to retract the curvable portion of the tamp into the first cannula and straightening the curvable portion within the first cannula.

14. The method of claim 13, wherein operating the tool hub to retract the curvable portion comprises rotating the rotatable collar of the tool hub to move the movable head of the tool hub away from the stationary cannula attachment of the tool hub, wherein the tamp is coupled to the movable head.

* * * * *